(12) United States Patent
O'Keefe et al.

(10) Patent No.: US 12,183,461 B2
(45) Date of Patent: Dec. 31, 2024

(54) DYNAMICALLY UPDATING PLATFORM FOR AGE-RELATED LIFESTYLE AND CARE DECISIONS WITH PREDICTIVE ANALYTICS

(71) Applicant: Roobrik, Inc., Greensboro, NC (US)

(72) Inventors: Nate O'Keefe, Durham, NC (US); Jessica Bloch-Schulman, Greensboro, NC (US); Anand Raman, Oak Ridge, NC (US); Kellie Rash, Cary, NC (US)

(73) Assignee: Roobrik, Inc., Greensboro, NC (US)

( * ) Notice: Subject to any disclaimer, the term of this patent is extended or adjusted under 35 U.S.C. 154(b) by 420 days.

(21) Appl. No.: 17/324,750

(22) Filed: May 19, 2021

(65) Prior Publication Data
US 2022/0375600 A1 Nov. 24, 2022

(51) Int. Cl.
*G16H 50/20* (2018.01)
*G06N 20/00* (2019.01)
*G16H 10/60* (2018.01)

(52) U.S. Cl.
CPC ............ *G16H 50/20* (2018.01); *G06N 20/00* (2019.01); *G16H 10/60* (2018.01)

(58) Field of Classification Search
None
See application file for complete search history.

(56) References Cited

U.S. PATENT DOCUMENTS

| | | | |
|---|---|---|---|
| 10,460,842 B1 | 10/2019 | Walker | |
| 10,853,455 B2 | 12/2020 | Foster et al. | |
| 11,240,329 B1 * | 2/2022 | Jain | G16H 20/10 |
| 11,482,330 B1 * | 10/2022 | Bosworth | G06N 20/00 |
| 11,636,500 B1 * | 4/2023 | Jain | G06N 20/00 705/7.32 |
| 12,020,814 B1 * | 6/2024 | McNair | G16H 50/70 |
| 2006/0293570 A1 | 12/2006 | Croghan et al. | |
| 2010/0159433 A1 * | 6/2010 | Graham | G09B 7/00 434/362 |
| 2013/0054260 A1 * | 2/2013 | Evans | G16H 10/60 705/2 |
| 2013/0179178 A1 | 7/2013 | Vemireddy et al. | |
| 2013/0191162 A1 | 7/2013 | Wons et al. | |

(Continued)

FOREIGN PATENT DOCUMENTS

WO  WO 2020/237300 A1 *  5/2020  ............... A61B 5/00

OTHER PUBLICATIONS

EHealth Initiatives for The Promotion of Healthy Lifestyle and Allied Implementation Difficulties; Chatterjee et al., Seventh International Workshop on e-Health Pervasive Wireless Applications and Services 2019.*

(Continued)

*Primary Examiner* — David J Stoltenberg
(74) *Attorney, Agent, or Firm* — NEO IP

(57) ABSTRACT

Systems and methods for a care decision platform operable to facilitate shared decision making for care services and/or lifestyle choices related to aging. The present invention incorporates medical decision aids, recommendation engines, and scoring algorithms to design a dynamically updating curriculum for improving customer outcomes as a result of care services and/or lifestyle choices. The curriculum is operable to be implemented as a customer relationship management tool for a care service provider.

20 Claims, 22 Drawing Sheets

(56) References Cited

U.S. PATENT DOCUMENTS

| | | | |
|---|---|---|---|
| 2013/0253942 A1* | 9/2013 | Liu | G16H 50/20 |
| | | | 705/2 |
| 2014/0006053 A1* | 1/2014 | Moen | G16H 10/60 |
| | | | 705/3 |
| 2015/0356701 A1* | 12/2015 | Gandy | G06Q 10/109 |
| | | | 705/2 |
| 2016/0055760 A1 | 2/2016 | Mirabile | |
| 2018/0068407 A1 | 3/2018 | Sicard et al. | |
| 2018/0322252 A1* | 11/2018 | Eggebraaten | G16H 20/40 |
| 2018/0374581 A1 | 12/2018 | Berringer et al. | |
| 2019/0333614 A1* | 10/2019 | Burger | A61B 5/02055 |
| 2019/0392924 A1* | 12/2019 | Bettencourt-Silva | |
| | | | G16H 50/70 |
| 2020/0143946 A1 | 5/2020 | Lewis | |
| 2021/0182750 A1* | 6/2021 | Brannon | G06F 21/577 |
| 2021/0319898 A1* | 10/2021 | Kapoor | G16H 30/20 |
| 2021/0343406 A1* | 11/2021 | McMillan | G06F 16/244 |
| 2022/0084664 A1* | 3/2022 | Ginsburg | G16H 15/00 |
| 2023/0045696 A1* | 2/2023 | Griffin | G16H 50/70 |

OTHER PUBLICATIONS

Tresp et al., Going Digital: A Survey on Digitalization and Large-Scale Data Analytics in Healthcare; vol. 104, No. 11, Nov. 2016 | Proceedings of the IEEE.*

* cited by examiner

| QUESTIONS/ANSWERS | | Pre-Completed Text | Support Group Label | Self-Checked | Guidance | Active | Edit | |
|---|---|---|---|---|---|---|---|---|
| Answer | | Pre-populated Text | Support Group Label | Self-Checked | Guidance | Active | Edit | Add Answer |
| Living at home with no help | | (recipient)> <lives at home without help> | Home w/ no help | | 50 | Active | Edit | |
| Living at home with help from a family member or friend | | (recipient)> <lives at home with help from family or friends> | Home w/ help from family/friends | | 50 | Active | Edit | |
| Living at home with some professional help | | (recipient)> <lives at home with some professional help> | Home w/ professional help | | 50 | Active | Edit | |
| Living in a senior living community, with no help | | (recipient)> <lives in a senior living community, without help> | SLC w/ no help | | 50 | Active | Edit | |
| Living in a senior living community that includes help | | (recipient)> <lives in a senior living community that includes help> | SLC w/ help | | 50 | Active | Edit | |
| Back to list | | | | | | | | |
| Cancel | Submit | | | | | | | |

Hi!

You recently completed a Roobrik assessment provided by a SageLife community called "Is it the right time for senior living?"

This is not an easy decision for most people, and it's not the *right* decision for everyone. We are here to help you think about your options and to tell you a little bit more about senior living, both the positives and negatives.

Today, we want to talk about the pros and cons of calling or visiting a community, even if you're still just researching your options. This post will help you think about whether it's the right time to talk to someone at a senior living community.

You're receiving this email because you recently completed a Roobrik assessment and shared your email address. You can unsubscribe at any time.

Roobrik

FIG. 8

DYNAMICALLY UPDATING PLATFORM FOR AGE-RELATED LIFESTYLE AND CARE DECISIONS WITH PREDICTIVE ANALYTICS

BACKGROUND OF THE INVENTION

1. Field of the Invention

The present invention relates to a care decision platform and more specifically to a care decision platform that creates a dynamic curriculum for engagement with care service providers and/or lifestyle choices.

2. Description of the Prior Art

It is generally known in the prior art to provide medical decision aid using a variety of inputs and information. Platforms for aggregating and analyzing medical data in order to provide treatment recommendations are described in the prior art. It is also generally known to develop medical recommendations based on new information to increase patient adherence and/or improve patient outcomes.

Prior art patent documents include the following:

U.S. Patent Publication No. 2018/0068407 for elder care assessment and interactive case management system by inventors Sicard, et al., filed Feb. 17, 2016 and published Mar. 8, 2018 for a system and methods for enabling care partners to collaborate and assess the level of care needed by a care recipient for whom they are responsible. The system provides a computer application accessible using a computing device that accesses a SaaS application over the Internet. The level of abilities and needs of the care recipient are assessed by one or more care partners and an overall level of care is determined in response to the assessment determined by the care partners and input into the computer application. Historical data and trends can be monitored over time. In addition, frailty and mood factors can be taken into consideration as well for adjusting the level of care needed by the care recipient.

U.S. Patent Publication No. 2016/0055760 for system and method for generating health and lifestyle observations and recommendations for an individual by inventor Mirabile, filed Mar. 27, 2015 and published Feb. 25, 2016, for a system and method for generating health and lifestyle related observations and recommendations for a user, based on information collected from the user. The system and method is configured to accept user inputs that include activity, physical, biological, environmental, subjective, goal, real-time and historical user information, inputted directly into the system, or via a third party integration. System and method references aggregated information across users and from additional sources, and generates relevant recommendations and observations, based on the system's computational methods applied to the user's inputs. The system and method considers the user's goals and system default goals in the generation of recommendations. The system and method allows for the data and generated observations and recommendations to be outputted within the system's user experience, or to a third party.

U.S. Patent Publication No. 2006/0293570 for method and apparatus for remotely enabled personal independence by inventors Croghan, et al., filed Jun. 24, 2005 and published Dec. 28, 2006, for methods and apparatus for in-residence care. The methods and apparatus enable a remote care provider to configure a home with a home controller and a plurality of medical and non-medical sensors based on the results of a periodic assessment survey. The remote care provider may also download software to the home controller to allow a new sensor to be connected to the home controller. The remote care provider then monitors data from the sensors electronically and provides services based on the assessment survey. Periodically and/or based on alerts generated in response to the monitored data, the remote care provider conducts virtual visits to the home using an audio/video telecommunications system. A home care provider or other professional may also conduct an actual visit to the home, and data associated with the actual visits may be recorded by the remote care provider.

U.S. Pat. No. 10,460,842 for interactive and analytical system that provides a dynamic tool for therapies to prevent and cure dementia-related diseases by inventor Walker, filed Jun. 30, 2015 and issued Oct. 29, 2019, for a computer-implemented method, system, and apparatus for providing interactive and analytical components that provide a comprehensive and dynamic tool for therapies to prevent and cure dementia-related diseases. The system includes one or more computers that receive and store personal information for people, including personal background information, pre-existing conditions, current medications, genomic data and diagnostic information. The computers also generate synergic data containing compounded probability data specifying an expected adjustment of individual biological mechanisms from particular combinations of therapies. For each person, the computers process personal information and identify a subset of biological mechanisms that are principally affected by dementia-related diseases or the substantial risk of dementia-related diseases. The computers also apply the personal information including the principally-affected biological mechanisms to the therapy data and generate for each person one or more messages communicating a therapy plan containing a combination of therapies and determines how to apply the therapies.

U.S. Pat. No. 10,853,455 for care management outreach by inventors Foster, et al., filed Dec. 30, 2014 and issued Dec. 1, 2020 for methods, systems, and computer-readable media for automatically generating outreach events for a care management service. Patient health data is received and processed to determine that a patient is eligible for care management services. Upon determining that the patient is eligible for care management services, a welcome-to-service template is selected, populated with patient-specific information, and communicated to the patient. The patient's health data is monitored to determine if there has been a change in care management status for the patient. Upon detecting a change in status, an appropriate template is selected, populated with patient-specific information, and communicated to the patient and/or a care team caring for the patient.

U.S. Patent Publication No. 2018/0374581 for hospitalization admission risk assessment tool and uses thereof by Berringer, et al., filed Dec. 15, 2016 and published Dec. 27, 2018 for a secure and automated computerized system providing a computerized program product and service method for integrating disparate data sources and assessing risk of hospital admission of an individual is disclosed. Individuals who are long-term residents of a nursing facility may be stratified into high, medium, or low risk groups, and the information used by health care service providers. The system also includes methods for providing an individualized resident "continuum of care" plan for a particular resident. A unique set of covariate elements for use in the automated computerized method and system is also provided.

U.S. Patent Publication No. 2013/0179178 for system and method for patient care plan management by inventors Vemireddy, et al., filed Jan. 6, 2012 and published Jul. 11, 2013 for a method and system for implementing patient care management functionality. The disclosure includes querying a set of clinical rules and obtaining claims data containing clinical information relating to a plurality of patients. The system can identify patients that would benefit from care management and create a listing of markers, or conditions, associated with each identified patient based on the claims data containing clinical information relating to the patient. The system generates an individual care plan for a patient base on the identified markers and the claims data containing clinical information relating to the patient.

U.S. Patent Publication No. 2020/0143946 for patient risk scoring and evaluation systems and methods by inventor Lewis, filed Nov. 4, 2019 and published May 7, 2020 for Systems and methods for increasing throughput of a case management system include receiving data associated with a user, determining predicted risk factors based on the user data, calculating a risk score based on the predicted risk factors, and administering a service that validates the predicted risk factors. The service includes a dynamically-generated questionnaire having an initial question associated with a prioritized predicted risk and a plurality of subsequent questions that are generated based on previous answers and an optimization function that minimizes a total number of questions needed for the service to validate the predicted risk factors. Systems and methods further include administering risk mitigation services corresponding to validated risk factors, updating the user data with data collected from administered services, and updating the risk score based on the updated data. Systems and methods can include updating the risk score to reflect determined non-risk factors.

U.S. Patent Publication No. 2013/0191162 for system and method for facilitating outcome-based health care by inventors Wons, et al., filed Feb. 18, 2013 and published Jul. 25, 2013 for a server receiving from a communication device (i) an identifier of a patient and (ii) a login credential associated with an individual. The server makes a determination based on the login credential that the individual is authorized to access a patient record of the patient. Subsequent to making the determination, the server prepares an assessment based on the patient record, and provides the assessment to the communication device. The assessment includes a measurement. The server subsequently receives a measurement result from the communication device and updates the patient record based on the measurement result. The server prepares a care plan based on the patient record and provides the care plan to the communication device. The care plan includes a task. The server subsequently receives a task status from the communication device and updates the patient record based on the task status.

SUMMARY OF THE INVENTION

The present invention relates to a care decision platform for facilitating shared decision making regarding care services and/or other age-related lifestyle choices. The care decision platform is operable to provide recommendations and/or a curriculum for engaging with care services. In another embodiment, the care decision platform is also operable to provide recommendations and/or a curriculum for lifestyle choices related to aging. Alternatively, the care decision platform is operable to provide recommendations and/or a curriculum for care services and non-care-related lifestyle choices.

It is an object of this invention to provide a dynamically updating curriculum and a virtual nurturing decision coach to facilitate interaction and relationship management between a user and a care service provider.

In one embodiment, the present invention is a system for engaging with care service options and/or lifestyle choices, including at least one user device, at least one cloud platform, an assessment platform, a data collection engine, a scoring engine, a recommendation engine, and a decision coach, wherein the at least one user device is operable for network communication with the at least one cloud platform, wherein the assessment platform is operable to administer at least one assessment to the at least one user account on at least one user device and receive assessment data in response to the at least one assessment, wherein the data collection engine is operable to collect passive data from the at least one user device and combine the passive data and the assessment data into user data, wherein the user data is in a standardized format, wherein the scoring engine is operable to generate at least one score based on the user data, wherein the recommendation engine is operable to generate at least one recommendation based on the user data, wherein the decision coach is operable to design a curriculum of next steps based on the user data, the at least one score, and the at least one recommendation, wherein the decision coach is operable to deliver the curriculum to the at least one user account on the at least one user device, wherein the decision coach is operable to dynamically adjust the curriculum based on updated user data, and wherein the at least one cloud platform is operable to store the user data and the curriculum.

In another embodiment, the present invention is a system for engaging with care service options and/or lifestyle choices, including at least one user device, at least one cloud platform, an assessment platform, a data collection engine, a scoring engine, a recommendation engine, and a decision coach, wherein the at least one user device is operable for network communication with the at least one cloud platform, wherein the assessment platform is operable to administer at least one assessment to at least two user accounts on the at least one user device and receive assessment data from the at least two user accounts in response to the at least one assessment, wherein the data collection engine is operable to collect passive data associated with each of the at least two user accounts from the at least one user device and combine the passive data and the assessment data into user data, wherein the user data is in a standardized format, wherein the scoring engine is operable to generate at least one score based on the user data, wherein the recommendation engine is operable to generate at least one recommendation based on the user data, wherein the decision coach is operable to design at least one curriculum of next steps based on the user data, the at least one score, and the at least one recommendation, wherein the decision coach is operable to deliver the at least one curriculum on the at least one user device, wherein the decision coach is operable to dynamically adjust the at least one curriculum based on updated user data, and wherein the at least one cloud platform is operable to store the user data and the at least one curriculum.

In yet another embodiment, the present invention is a method for engaging with care service options and/or lifestyle choices, including an assessment platform administering at least one assessment to at least one user account on at least one user device and receiving assessment data in response to the at least one assessment, a data collection engine collecting passive data from the at least one user device and combining the assessment data and the passive data into user data, wherein the user data is in a standard format, a scoring engine generating at least one score based on the user data, a recommendation engine generating at least one recommendation based on the user data, a decision coach designing at least one curriculum of next steps based on the user data, the at least one score, and the at least one recommendation, the decision coach delivering the at least one curriculum on the at least one user device, the decision coach dynamically adjusting the at least one curriculum based on updated user data, and at least one cloud platform storing the user data and the at least one curriculum, wherein the at least one user device is in network communication with the at least one cloud platform.

These and other aspects of the present invention will become apparent to those skilled in the art after a reading of the following description of the preferred embodiment when considered with the drawings, as they support the claimed invention.

BRIEF DESCRIPTION OF THE DRAWINGS

FIG. 1 illustrates an embodiment of the assessment platform of the present invention.

FIG. 2A illustrates an alternate view of the assessment platform of the present invention.

FIG. 2B illustrates an alternate view of the assessment platform of the present invention.

FIG. 5 illustrates an embodiment of an interface of the present invention.

FIG. 8 illustrates an example embodiment of a communication of the present invention.

DETAILED DESCRIPTION

Figure 3A:
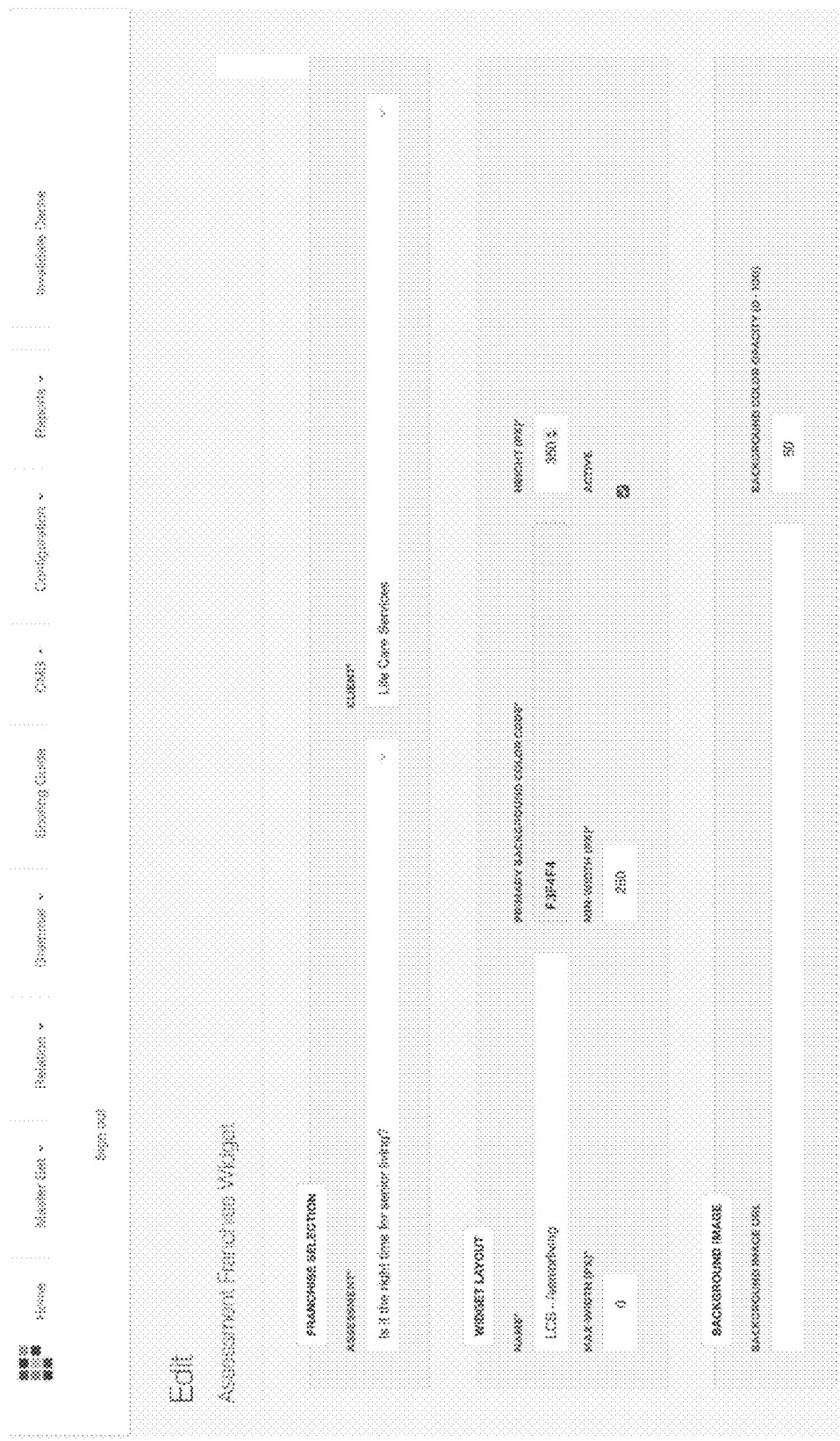
FIG. 3A illustrates an example embodiment of the care decision platform of the present invention.

The present invention is generally directed to systems and methods for a care decision platform operable to facilitate shared decision making for care services and/or lifestyle choices related to aging. The present invention incorporates medical decision aids, recommendation engines, and scoring algorithms to design a dynamically updating curriculum for improving customer outcomes in care services. The curriculum is operable to be implemented as a customer relationship management tool for a care service provider. In a preferred embodiment, the customer is an elderly person, and the care services are senior care services. The lifestyle choices are best suited for elderly populations and are customized for the specific needs and preferences of the customer.

In one embodiment, the present invention is a system for engaging with care service options, including at least one user device, at least one cloud platform, an assessment platform, a data collection engine, a scoring engine, a recommendation engine, and a decision coach, wherein the at least one user device is operable for network communication with the at least one cloud platform, wherein the assessment platform is operable to administer at least one assessment to the at least one user account on at least one user device and receive assessment data in response to the at least one assessment, wherein the data collection engine is operable to collect passive data from the at least one user device and combine the passive data and the assessment data into user data, wherein the user data is in a standardized format, wherein the scoring engine is operable to generate at least one score based on the user data, wherein the recommendation engine is operable to generate at least one recommendation based on the user data, wherein the decision coach is operable to design a curriculum of next steps based on the user data, the at least one score, and the at least one recommendation, wherein the decision coach is operable to deliver the curriculum to the at least one user account on the at least one user device, wherein the decision coach is operable to dynamically adjust the curriculum based on updated user data, and wherein the at least one cloud platform is operable to store the user data and the curriculum.

In one embodiment, the at least one user device is a wearable device, a mobile device, a tablet, a computer, a smart speaker, and/or a smart phone. In another embodiment, the user data further includes sensor data. In one embodiment, the user data further includes electronic health record (EHR) data, and the data collection engine is operable to integrate with an EHR platform. In one embodiment, the data collection engine is operable to apply at least one filter to the user data. The filter is used to remove data that is irrelevant to the calculation of the at least one score. Alternatively, the filter is used to determine which data is most accurate for the calculation of the at least one score. In one embodiment, the passive data includes web analytics, urchin tracking module (UTM) parameters, date, time, online user behaviors, a completion rate, engagement metrics, response distribution, hypertext markup language (HTML) requests, and/or location information. In one embodiment, the at least one score is a readiness for a care service option. In one embodiment, the decision coach is operable to selectively present a portion of the curriculum to the user. In one embodiment, the assessment platform is operable to prompt the user for the updated user data according to a schedule. In one embodiment, the decision coach is operable to correlate a plurality of input data points with a plurality of outcome data points to design and/or adjust the curriculum. In another embodiment, the decision coach is operable to design and/or adjust the curriculum using at least one machine learning algorithm. Alternatively, the decision coach is operable to design and/or adjust the curriculum using at least one predictive analytics model. In one embodiment, the decision coach is further operable to design and/or adjust the curriculum using past user outcomes data. In one embodiment, the curriculum includes a plurality of paths wherein the decision coach is operable to choose one of the plurality of paths based on the updated user data. In one embodiment, the decision coach is operable to adjust the curriculum based on the updated user data in real time or near-real time.

In another embodiment, the present invention is a system for engaging with care service options, including at least one user device, at least one cloud platform, an assessment platform, a data collection engine, a scoring engine, a recommendation engine, and a decision coach, wherein the at least one user device is operable for network communication with the at least one cloud platform, wherein the assessment platform is operable to administer at least one assessment to at least two user accounts on the at least one user device and receive assessment data from the at least two user accounts in response to the at least one assessment, wherein the data collection engine is operable to collect passive data associated with each of the at least two user accounts from the at least one user device and combine the passive data and the assessment data into user data, wherein the user data is in a standardized format, wherein the scoring engine is operable to generate at least one score based on the user data, wherein the recommendation engine is operable to generate at least one recommendation based on the user data, wherein the decision coach is operable to design at least one curriculum of next steps based on the user data, the at least one score, and the at least one recommendation, wherein the decision coach is operable to deliver the at least one curriculum on the at least one user device, wherein the decision coach is operable to dynamically adjust the at least one curriculum based on updated user data, and wherein the at least one cloud platform is operable to store the user data and the at least one curriculum.

In one embodiment, the decision coach is operable to deliver the at least one curriculum to each of the at least two users simultaneously. In one embodiment, the decision coach is operable to design and adjust an aggregate curriculum based on the user data, the at least one score, and the at least one recommendation.

In yet another embodiment, the present invention is a method for engaging with care service options, including an assessment platform administering at least one assessment to at least one user account on at least one user device and receiving assessment data in response to the at least one assessment, a data collection engine collecting passive data from the at least one user device and combining the assessment data and the passive data into user data, wherein the user data is in a standard format, a scoring engine generating at least one score based on the user data, a recommendation engine generating at least one recommendation based on the user data, a decision coach designing at least one curriculum of next steps based on the user data, the at least one score, and the at least one recommendation, the decision coach delivering the at least one curriculum on the at least one user device, the decision coach dynamically adjusting the at least one curriculum based on updated user data, and at least one cloud platform storing the user data and the at least one curriculum, wherein the at least one user device is in network communication with the at least one cloud platform.

None of the prior art discloses a dynamically updating curriculum for improving customer outcomes as a result of aging-related lifestyle decisions. It is known in the prior art to use a plurality of input data points to design a care plan. However, the present invention designs a curriculum with a plurality of path decisions. The present invention further includes a decision coach wherein the decision coach is operable to execute nurturing steps according to the dynamically adjusting curriculum. The nurturing steps improve customer outcomes and customer relationships.

In one embodiment, the present invention includes a care decision platform including at least one scoring engine, at least one recommendation engine, and a decision coach. In one embodiment, the present invention is operable to be used by a customer in order to determine best next steps for care services and/or lifestyle choices. Alternatively, the present invention is operable to determine best next steps for a care service provider. The care decision platform is operable to collect customer data regarding a customer of a care service provider from a plurality of stakeholders. Advantageously, the customer data includes not only quantitative data but also qualitative data including readiness metrics and areas of concern specific to the customer. The at least one scoring engine is then operable to aggregate and analyze the customer data collected by the care decision platform in order to assess the fitness of a plurality of solutions and/or next steps for the customer, thereby creating at least one customer score. The at least one recommendation engine is operable to determine at least one recommendation for a next step wherein the next step is likely to lead to future engagement and improved outcomes for both the customer and the care service provider. In a preferred embodiment, the care decision platform creates a custom curriculum for the care service provider and the customer. The curriculum includes recommendations, next steps, a timeline, and/or alternative conditional steps. The decision coach is operable to facilitate the delivery of the curriculum to the customer.

In one embodiment, the care decision platform is operable to use data from the care service provider to create the at least one score, the recommendation, and the curriculum. In one embodiment, the care decision platform is also operable to incorporate principles of behavior science and customer relationship management in order to create the at least one customer score and the curriculum. The care decision platform is further operable to modify, update, and/or override the curriculum based on new data. Advantageously, the care decision platform is operable to track engagement between the customer and the care service provider and modify the at least one customer score and the curriculum in order to improve outcomes for both the customer and the care service provider. In an example embodiment, the customer is an elderly person and the care service provider is a senior care provider. The curriculum addresses age-related lifestyle choices for the elderly, including but not limited to living conditions and/or location, community options, assistance, habits, nutrition, mobility, fitness, leisure and recreation, health decisions, treatment options, visitation options, and/or lifestyle recommendations.

The care decision platform is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The care decision platform is operable to use any of the aforementioned learning techniques alone or in combination.

Further, the care decision platform is operable to utilize predictive analytics techniques including, but not limited to, machine learning (ML), artificial intelligence (AI), neural networks (NNs) (e.g., long short-term memory (LSTM) neural networks), deep learning, historical data, and/or data mining to make future predictions and/or models. The care decision platform is preferably operable to recommend and/or perform actions based on historical data, external data sources, ML, AI, NNs, and/or other learning techniques. The platform is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Referring now to the drawings in general, the illustrations are for the purpose of describing one or more preferred embodiments of the invention and are not intended to limit the invention thereto.

Data Collection

In one embodiment, the care decision platform collects customer data about the customer. The customer data includes but is not limited to data about the customer's daily habits, living environment, demographics, family history, mobility, cognitive functions, medical history, medication information, observed behaviors, current interventions, and/or social determinants of health. Social determinants of health include but are not limited to financial stability, physical environment, education, nutrition, community and social context, documentation status, race, gender, and/or sexual orientation. The customer data further includes but is not limited to data about the customer's opinions and understanding of care service options and/or age-related lifestyle changes, concerns and anxieties, readiness to act, financial concerns, health concerns, values, and/or preferences. In a preferred embodiment, the care decision platform administers an assessment to collect assessment data from the customer via an assessment platform. The assessment is operable to be administered by the assessment platform on a computer, e.g., on a website. Alternatively, the assessment is operable to be administered on a mobile device and/or a tablet, e.g., on an app. In yet another embodiment, the care decision platform is operable to collect the assessment data and other customer data via audio input and/or a voice-operated device including but not limited to a Google Home, Amazon Echo, Facebook Portal, and/or Apple HomePod. The assessment platform is further operable to incorporate audio analytics in order to detect a user's emotional and/or mental state based on interactions with the voice-operated device. In one embodiment, the care decision platform is operable to collect data from electronic health records (EHR) and other medical records. In one embodiment, the assessment platform is operable to be integrated with an EHR system.

Figure 2A:
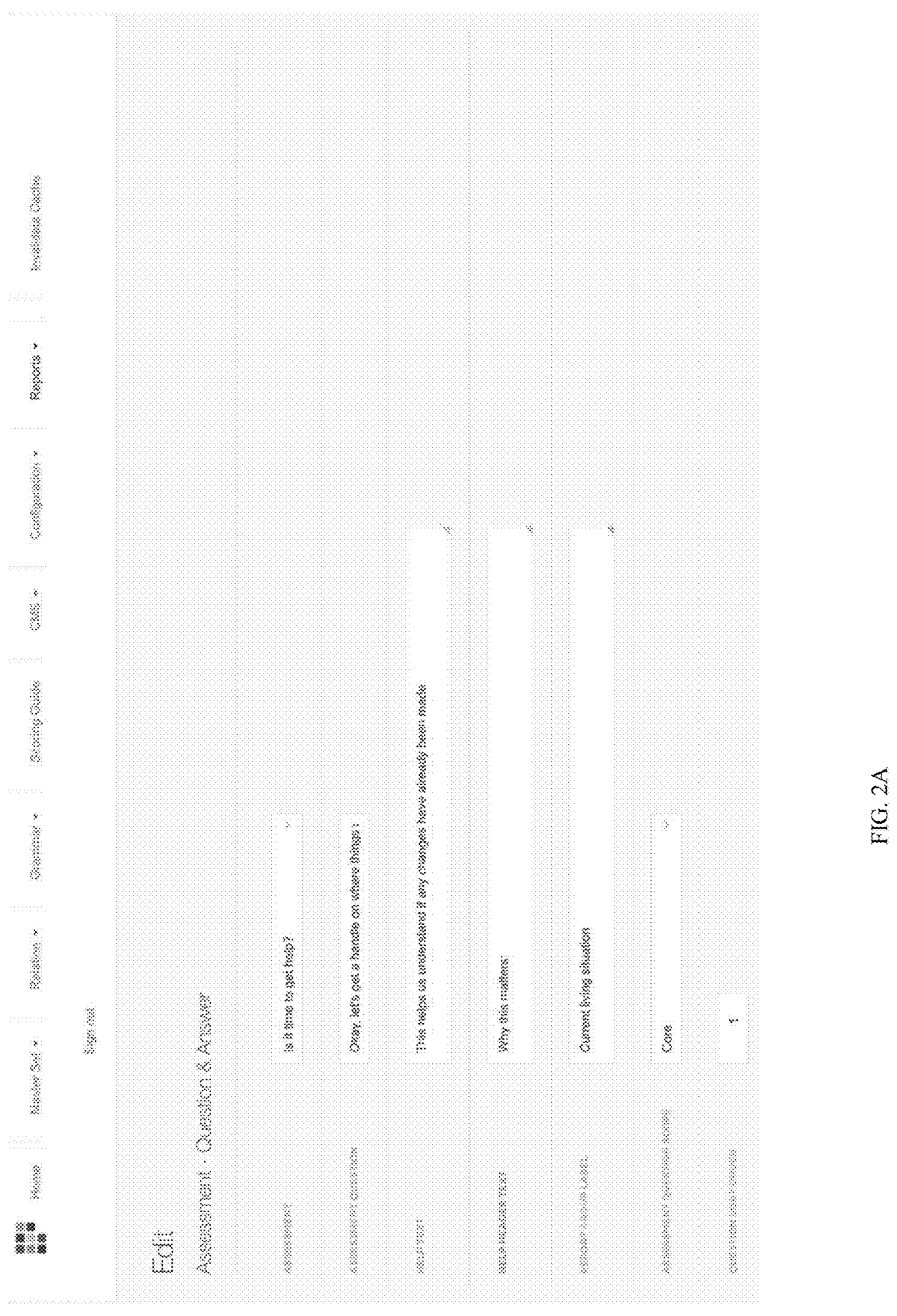

In one embodiment, the assessment is a general assessment regarding care services. In another embodiment, the assessment platform includes a plurality of customer assessments, wherein each of the customer assessments focuses on one type of care service or age-related lifestyle question. Example questions include but are not limited to whether the customer should consider home care, whether the customer should consider senior living, whether clinical research is appropriate for the customer, whether the customer should continue driving, whether the customer has dementia, and/or whether the customer should seek help. In one embodiment, the assessment platform includes a question library wherein an assessment is operable to be created and customized using the question library by a care service provider. FIG. 1 illustrates an embodiment of the assessment platform wherein the assessment platform is operable to administer multiple assessments. FIG. 2A illustrates an alternative view of the assessment platform wherein the title, the description, and the type of assessment are operable to be customized. FIG. 2B illustrates an embodiment of the assessment platform wherein the answers to the assessment are operable to be customized to adapt to the answers and/or configurations of the customer.

In one embodiment, the care decision platform is operable to collect the customer data from the customer themselves. In another embodiment, the care decision platform is operable to collect the customer data from a stakeholder capable of providing the customer data. The customer data collected by the care decision platform in this embodiment further includes data about the stakeholder, including but not limited to preferences, interests, views, concerns, financial data, a relationship with the customer, and/or observations of customer behavior. In another embodiment, the care decision platform is operable to collect the customer data from a plurality of stakeholders. As a non-limiting example in a senior care services embodiment, the care decision platform is operable to collect data about the customer from a plurality of stakeholders including an adult child of the customer and a caretaker of the customer. The care decision platform is then operable to highlight results based on the inputs of the plurality of stakeholders. In the case that the customer data from the plurality of stakeholders is conflicting and/or contradictory, the care decision platform is operable to automatically highlight areas of assent and dissent, provide strategies for mediating the areas of dissent, provide strategies for expediting decision-making, and/or resolve the areas of dissent. In one embodiment, the care decision platform is operable to incorporate aggregate data, historical customer outcomes data, and/or predictive analytics to make recommendations for resolving areas of dissent. The recommendations are based on previously effective steps for resolving areas of dissent. In one embodiment, the care decision platform is operable to encourage additional stakeholders to participate in data collection and/or decision making.

In one embodiment, the care decision platform includes a data collection engine. The data collection engine is operable to collect passive customer data and/or metadata when a user (e.g., a customer, a stakeholder) is interacting with the care decision platform. The passive customer data includes but is not limited to web analytics, urchin tracking module (UTM) parameters, date, time, duration of usage, pacing, user behaviors, content displayed, online behaviors associated with partner platforms and sites, online behaviors associated with platforms and sites not associated with the care decision platform, online behaviors generally available, completion rate, engagement metrics, response distribution, metadata, and/or location information. In another embodiment, the care decision platform is operable to create and/or monitor cookies as part of the customer data. The cookies include but are not limited to first party cookies, third party cookies, and/or flash cookies. Alternatively, the care decision platform is operable for internet protocol (IP) fingerprinting, respawning, hybrid cookie management, cross-device tracking, local storage storing and/or reading, user registration, unique identifier creation and/or monitoring, and/or API integration to accomplish cookie functions (e.g., Google's Privacy Sandbox). As a non-limiting example, the care decision platform is operable to detect when the user spends a long period of time answering one question in an assessment and determine if additional follow-up questions about the same topic are required based on the customer data. Advantageously, the data collection engine is also operable to ingest customer analytics and data derived from customer usage of sites, platforms, and systems outside of the care decision platform. In one embodiment, the data collection engine collects external data via an API. Alternatively, the data collection engine is operable to collect and/or license data from a data warehouse. The care decision platform is operable to incorporate the passive customer data and/or metadata into the customer data. In one embodiment, the care decision platform is operable to incorporate the passive customer data and/or metadata with assessment data and the customer data into a standard format. In one embodiment, the standard format is a user profile wherein the user profile includes the assessment data, the passive customer data and/or metadata, usage data, and augmented data. In one embodiment, the care decision platform is operable to automatically scrub the passive customer data and the assessment data to extract the information needed for the standard format. In one embodiment, the standard format is operable to be changed based on new data. In one embodiment, user profile data is stored in a single database. Alternatively, the user profile data is usable across multiple databases via API integrations.

In one embodiment, the data collection engine is operable to collect the passive customer data, e.g., the web analytics data, from the user device. The data collection engine is operable to register actions and/or events taken on the user device when the user device is interacting with the care decision platform. Alternatively, the data collection engine is operable to register actions and/or events taken on the user device when the user device is not interacting with the care decision platform. The registration of the actions and/or events includes the timing and/or the sequence of the actions and/or events. The actions and/or events include but are not limited to clicks, screen time, web navigation events, web requests (e.g., HTTP requests), searches, search results, cookies, page sequences, and/or engagement. In one embodiment, the data collection engine is operable to parse web server logs wherein the web server logs include but are not limited to records of HTTP requests, timestamps, internet protocol (IP) addresses, and/or web client details. In one embodiment, the passive customer data include semantic context.

In one embodiment, the data collection engine is operable to automatically categorize the passive customer data as a specific type of action and/or event. In one embodiment, the care decision platform is operable to implement a categorization scheme based on input from the care service provider. Alternatively, the categorization scheme is implemented and updated by the care decision platform. The categorization scheme is operable to include at least one filter for the events and/or the actions. Alternatively, the categorization scheme includes rules for disregarding the recording of an action and/or event. In one embodiment, the data collection engine is further operable to categorize, analyze, and/or aggregate the passive customer data into user actions and/or events. The user actions and/or events are broader categorizations and interpretations of the actions and/or events. As a non-limiting example, the data collection engine records a plurality of HTTP requests, web navigation events, clicks, and screen time data while a user is filling out an assessment administered by the assessment platform. The data collection engine then analyzes the actions and/or events and determines that the user device completed the assessment and as well as how much screen time the user device spent on each question, and/or other websites and searches the user device ran while responding to each question on the assessment. This data is then used in part to determine the accuracy of the assessment data, further assessments that should be administered by the assessment platform, and/or next steps to be recommended by a recommendation engine. In one embodiment, the data collection engine incorporates machine learning techniques to categorize and analyze the passive customer data. In one embodiment, the data resulting from the analysis is augmented data. The data collection engine is also operable to use historical data in analyzing the passive customer data.

In one embodiment, the data collection engine is operable to determine the location of the user device. In one embodiment, the data collection engine is operable to collect and analyze sensor data from the user device in order to determine the location of the user device. The sensor data includes but is not limited to accelerometer data, magnetometer data, gyroscope data, barometer data, ambient light data, proximity sensor data, temperature data, humidity data, WIFI signal data, radiofrequency signal data, depth sensor data, an image, a video, an audio recording, visual odometry data, and/or "virtual sensor" data taken from the combination of two or more of the above-mentioned types of sensor data. In another embodiment, the data collection engine is operable to access global positioning system (GPS) data on the user device in order to determine the location of the user device. In yet another embodiment, the data collection engine is operable to determine the location of the user device using the proximity of the user device to a cell tower, e.g., by using a cell identification (cell ID), wherein the cell ID is used to identify a base station in proximity to the user device. Alternatively, the data collection engine is operable to determine the location of the user device using an application programming interface (API), e.g., a Hyper Text Markup Language (HTML) API, wherein the data collection engine is operable to call a geolocation API.

In one embodiment, the data collection engine is operable to collect customer data from at least one wearable device and/or at least one sensor. The at least one wearable device includes but is not limited to a smart watch, a fitness band, smart jewelry, an activity tracker, an implantable loop recorder, and/or a fall detector. The at least one sensor includes but is not limited to a heart rate sensor, a temperature sensor, a step counter, a scale, a body composition monitor, a motion detector, a blood oxygen monitor, a blood pressure sensor, a blood sugar meter, and/or a voice analyzer. The data collection engine is operable to collect the data from the at least one wearable device and/or at least one sensor on a regular basis. In another embodiment, the data collection engine collects the data from the at least one wearable device and/or the at least one sensor as part of an ongoing workflow of interaction between the care decision platform and the user.

Scoring Engine

The scoring engine of the present invention is operable to determine at least one score for the customer based on the customer data including the assessment data and the passive data. In one embodiment, the scoring engine is operable to determine a plurality of scores wherein each score in the plurality of scores addresses a different metric. Metrics include but are not limited to readiness for a care option (e.g., at-home care, downsizing, assisted living, skilled care, custodial care, memory care, virtual care, day care, palliative care, hospice care, and/or residential care), readiness for a community option (e.g., independent living, independent living with added services, assisted living, assisted living with added services, memory care, and/or skilled nursing), fitness for a care option, fitness for a community option, fitness for a lifestyle choice, a risk assessment, a probability of success, a probability of action, a probability of conversion, and/or a probability of commitment. In one embodiment, the at least one score is a range. In an alternative embodiment, the at least one score is a scaled score. The at least one score is a quantitative measure of the question posed in each customer assessment. In one embodiment, the at least one score is an aggregate score that combines a plurality of metrics, e.g., readiness and a level of care.

In one embodiment, the scoring engine uses at least one algorithm to determine the at least one score. In one embodiment, the at least one algorithm includes a weighting scheme. Alternatively, the scoring engine uses predictive analytics to determine the at least one score for the customer. In one embodiment, the scoring engine is operable to build a predictive model to determine the at least one score. In another example, the scoring engine is operable to build a descriptive model to determine the at least one score. Alternatively, the scoring engine is operable to build a decision model to determine the at least one score. The predictive analytics includes the customer data as well as historical and/or current data from the care service provider. For example, the scoring engine is operable to calculate a readiness score for an assisted living option for a customer based on decisions and outcomes of other customers of the care service provider with similar conditions and medical histories. In the embodiment wherein the care decision platform collects customer data from a plurality of stakeholders, the scoring engine is operable to generate an aggregate score using the customer data from the plurality of stakeholders. In one calculation method, the aggregate score is weighted according to each stakeholder. In an alternative embodiment, the scoring engine is operable to generate a different score for each stakeholder addressing the same metric.

As a non-limiting example, the at least one algorithm determines a score for whether a customer needs minimal, low, moderate, elevated, or around-the-clock levels of care. The at least one algorithm uses responses to assessment questions to determine the score. For example, each response to an assessment question is assigned a numerical score and a level of care wherein the level of care corresponds to a numerical range that encompasses the numerical score. In one embodiment, the numerical scores and the numerical ranges are based on a combination of historical customer outcomes data and/or clinical research data. In one embodiment, the at least one algorithm weights a portion of the assessment questions in the score calculation. Alternatively, the at least one algorithm weights a portion of response options for a portion of the assessment questions differently. The at least one algorithm then uses the numerical scores to determine a final score, wherein the final score corresponds to an appropriate level of care for the customer based on the customer data and the assessment. The final score is in one embodiment based on a combination of a numerical score and the presence or absence of specific pieces of customer data.

Recommendation Engine

The recommendation engine of the present invention is operable to determine at least one next step for the customer and the care service provider based on the customer data and the scoring engine. The at least one next step includes but is not limited to a medical assessment, a tour, a consultation, a communication, a follow-up, a trial, a lifestyle choice, and/or further data collection. The follow-up includes but is not limited to a reminder, a phone call, an email, a letter, an in-person meeting, a video call, an appointment, an offer for sale, a contract, and/or a completed sale. Alternatively, the follow-up includes enrollment in a campaign and/or advertising program operable to deliver targeted advertising and nurturing. The recommendation engine is operable to integrate medical decision aid options with customer engagement options to determine the steps that will result in improved outcomes for the customer and the care service provider.

The recommendation engine is operable to utilize historical customer outcomes data in determining the at least one next step. In one embodiment, the recommendation engine is operable to assess a plurality of next steps and the likely outcomes of each of the plurality of next steps based on the customer data as well as historical data about the care service provider and previous customers. As a non-limiting example, the recommendation engine recommends a next step that is likely to result in the customer signing a contract with the care service provider based on the customer data and historical data related to previous customers who have signed a contract with the care service provider. In one embodiment, the recommendation engine is operable to determine a series of steps to be followed in sequence. In another embodiment, the recommendation engine is operable to determine conditional steps depending on future customer behavior. In one embodiment, the recommendation engine is operable to customize the recommendations according to data about the care provider, including but not limited to services provided, resident demographic data, a physical location, sales goals, and/or occupancy goals. The recommendation engine is operable to integrate the at least one score determined by the scoring engine with recommendation options to determine the next steps.

Curriculum Design

The care decision platform is operable to integrate the scoring engine and the recommendation engine to create a custom curriculum for a customer based on the customer data. The curriculum is longitudinal in that it includes a plurality of next steps to be taken over time. In one embodiment, the curriculum is directed to a care provider and includes a timeline for delivering each next step in order to increase customer engagement and customer conversion. The curriculum is preferably designed to optimize health outcomes for the customer, customer engagement with the care service provider, and customer satisfaction. In one embodiment, the curriculum includes a plurality of paths wherein each path is dependent on at least one condition. In one embodiment, the at least one condition is a customer response. Alternatively, the at least one condition is a provider condition determined by the care service provider. The provider condition includes availability data, a pricing scheme, a schedule, a capacity, staffing concerns, budgets, availability of services, resident demographic data, sales goals, occupancy goals, a physical location, and/or other resources. In one embodiment, the curriculum includes medical decision recommendations. Alternatively, the curriculum includes financial recommendations and/or a financial plan for the customer.

In one embodiment, the curriculum is provided to a customer and facilitates shared decision making for the customer using a customized path. The curriculum enables the customer to understand their current condition, recognize that at least one next step is necessary, evaluate potential next steps, evaluate pros and cons of the potential next steps, communicate with a care service provider, and execute the at least one next step. The curriculum takes into account customer goals, including but not limited to preferences, values, a readiness, a treatment burden, an independence level, financial goals, physical wellbeing goals, mental wellbeing goals, social goals, and/or community goals. In one embodiment, the care decision platform incorporates principles of medical decision sciences and/or behavioral psychology in designing the curriculum. The curriculum includes but is not limited to steps and/or recommendations for contacting a care service provider, receiving a care service, seeking medical attention, receiving medical attention, building community, moving, communicating with a desired party, achieving a desired level of self-sufficiency, and/or achieving a health goal. Alternatively, the curriculum further includes lifestyle steps and/or recommendation addressing nutrition, fitness, living situation, living location, financial status, financial goals, social situation, leisure, recreation, physical health, mental health, and/or spiritual health.

In one embodiment, the curriculum includes predictive metrics and/or rates regarding customer outcomes. The customer outcomes include but are not limited to a contact, a follow-up, a tour, a pre-sale engagement, a sales process milestone, a sale engagement, a contract date, a move-in, a duration of sales funnel processes, a fitness for a care option, a fitness for a service, a level of care needed, a type of intervention, preferred amenities, a geographical location of care, a response distribution, health outcomes, a cognitive status, and/or a life expectancy. The level of care needed is measurable in hours, number of staff, and/or amount of coverage. In one embodiment, the curriculum includes recommendations for changing the predictive metrics around the customer outcomes, e.g., increasing the likelihood that the customer fulfills one of the customer outcomes. In another embodiment, the curriculum includes recommendations for changing, e.g., increasing, the fitness of the customer for a product or a service.

The curriculum is operable to use the predictive metrics as well as the customer data to dynamically adapt end user experience to achieve the goals of the customer as well as the care service provider. The end user experience includes but is not limited to content presented to the customer, questions asked to the customer, product recommendations, service recommendations, programs, and/or other communications with the customer. The care decision platform is operable to correlate a plurality of input data points with a plurality of outcome data points in order to develop the curriculum. In one embodiment, the curriculum includes product, service, and product recommendations for the customer based on the customer data. Alternatively, the curriculum recommends custom engagement strategies and/or custom product configurations for a care service provider partner working with the customer.

In one embodiment, the steps of the curriculum for each customer are determined using current customer data and historical data. The historical data includes but is not limited to data about the care service provider, data about the care decision platform, customer medical data, and/or customer behavioral data. The data about the care service provider includes but is not limited to customer outcomes data for past and present customers, e.g., historical customer outcomes data. The care decision platform uses the customer outcomes data and past curricula for customers with similar medical histories to design the curriculum for a current customer. Outcomes of previous curricula are used to determine the curriculum for the current customer. In one embodiment, the care decision platform includes a learning engine wherein the learning engine is trained on the previous curricula and the resulting outcomes in order to determine the curriculum for the current customer given the current customer data. The care decision platform is further operable to include a plurality of paths in the curriculum based on the historical data wherein the next step in each path depends on an outcome of a preceding step.

Customer Relationship Management

Figure 3B:
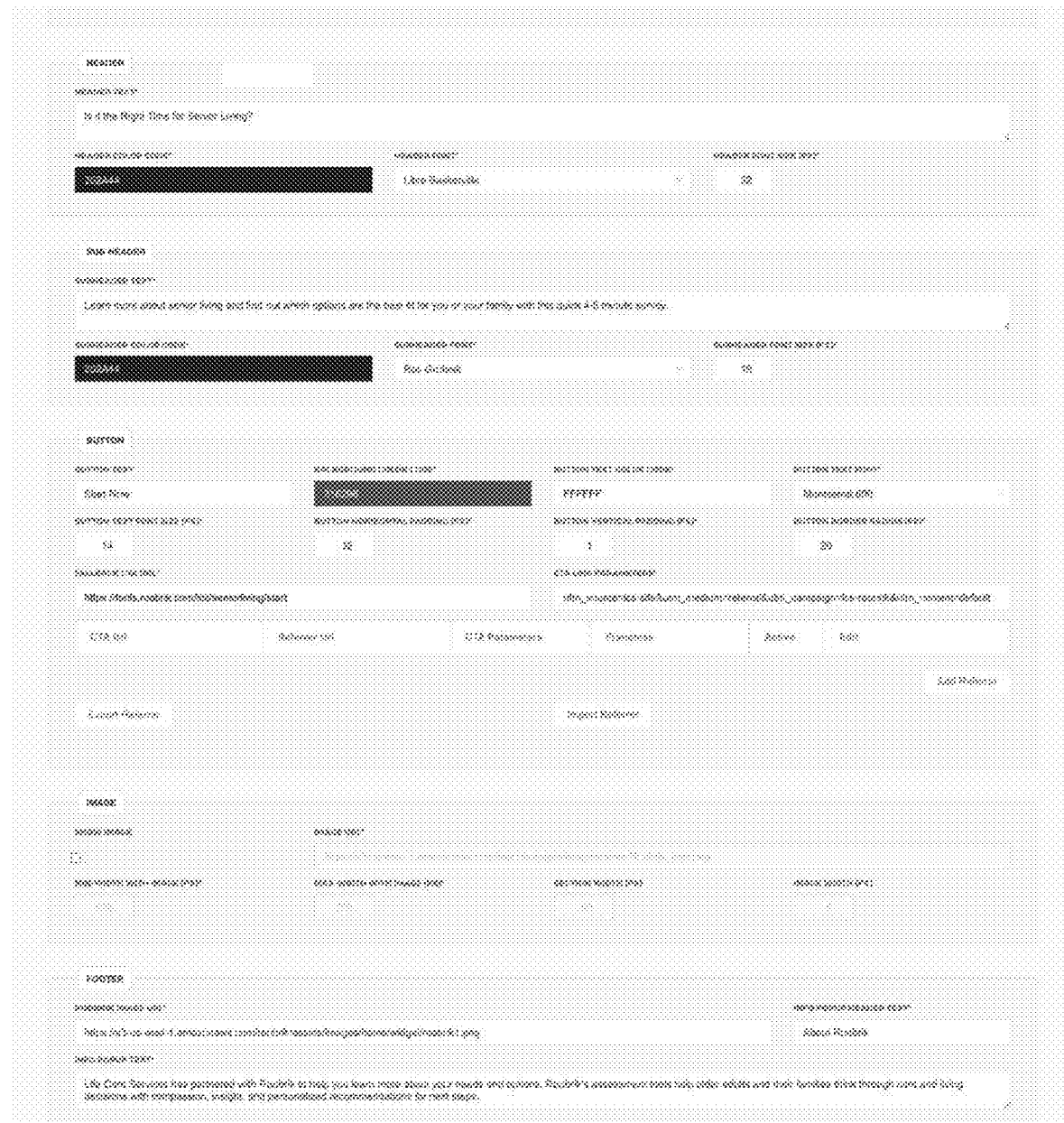
FIG. 3B illustrates an example embodiment of the care decision platform of the present invention.
Figure 3C:
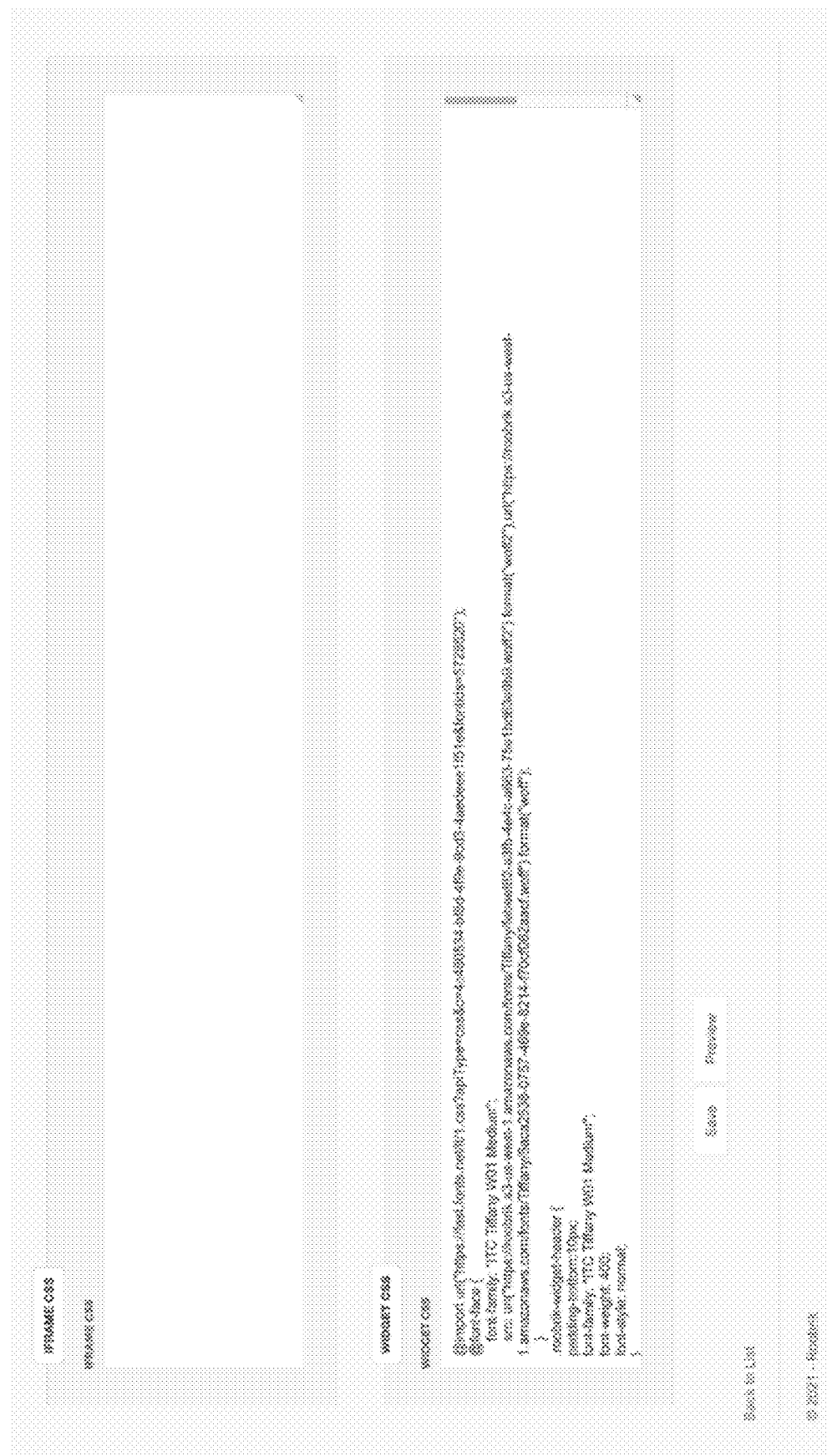
FIG. 3C illustrates an example embodiment of the care decision platform of the present invention.

The platform of the current invention is operable to be used as a customer relationship management (CRM) tool for the care service provider. The platform is operable to be integrated into the end user experience provided by the care service provider. In one embodiment, the platform is operable to be customized to the needs of the care service provider. Customizations include but are not limited to changes in logo, color palette, branding, visual indicators, skins, descriptions, results page imagery, call to action design, offerings, linked pages, advertisements, distribution method, question types, and/or custom questions. FIG. 3A illustrates one example embodiment wherein the care decision platform includes at least one customization widget and wherein the at least one customization widget is operable to customize the appearance and wording of the care decision platform for a franchise. FIG. 3B illustrates an embodiment wherein the at least one customization widget is operable to customize a header, a button, an image, and a footer. FIG. 3C illustrates an embodiment wherein the at least one customization widget is operable to customize the backend. In one embodiment, the present invention is operable to assess the existing systems and/or platforms of the care service provider and automatically adapt to be easily integrated with the care service provider. In another embodiment, the care service provider is operable to select and/or customize the adaptations of the care decision platform. The platform is further operable to be customized and/or personalized based on each customer. As a non-limiting example, a customer inputs their gender identity at the beginning of a survey. The pronouns used thereafter in the survey questions match the gender identity provided by the customer. In one embodiment, the assessment platform is operable to customize questions presented to a customer based on EHR data corresponding to the customer.

Figure 4A:
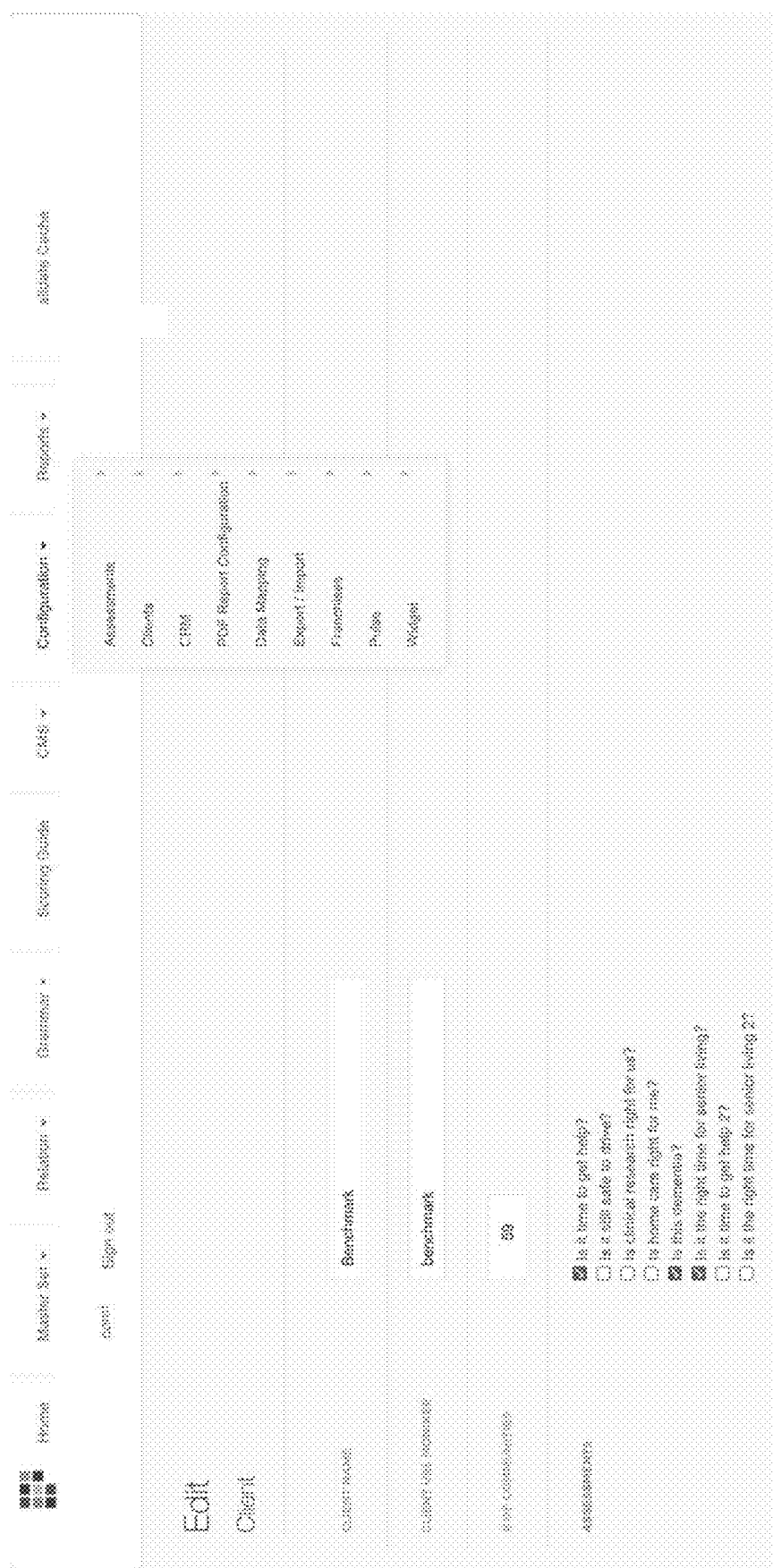
FIG. 4A illustrates an alternative embodiment of the care decision platform of the present invention.
Figure 4B:
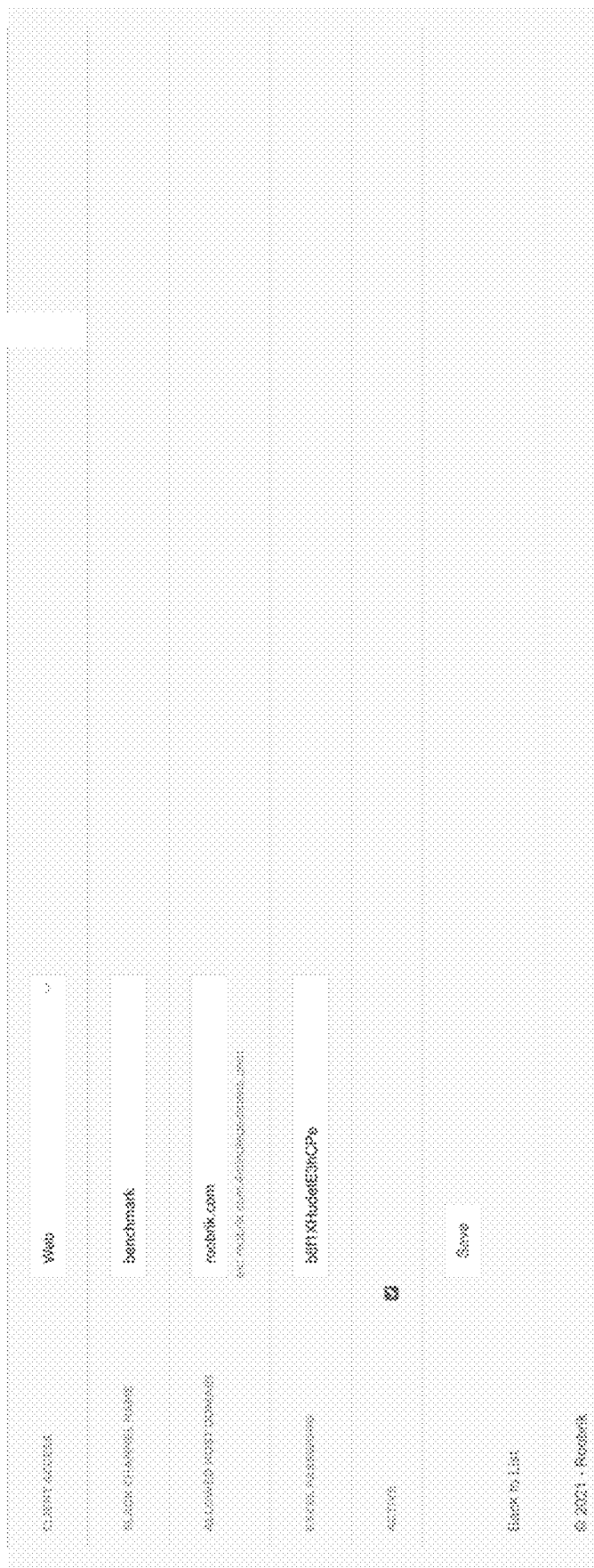
FIG. 4B illustrates an alternative embodiment of the care decision platform of the present invention.
Figure 5:
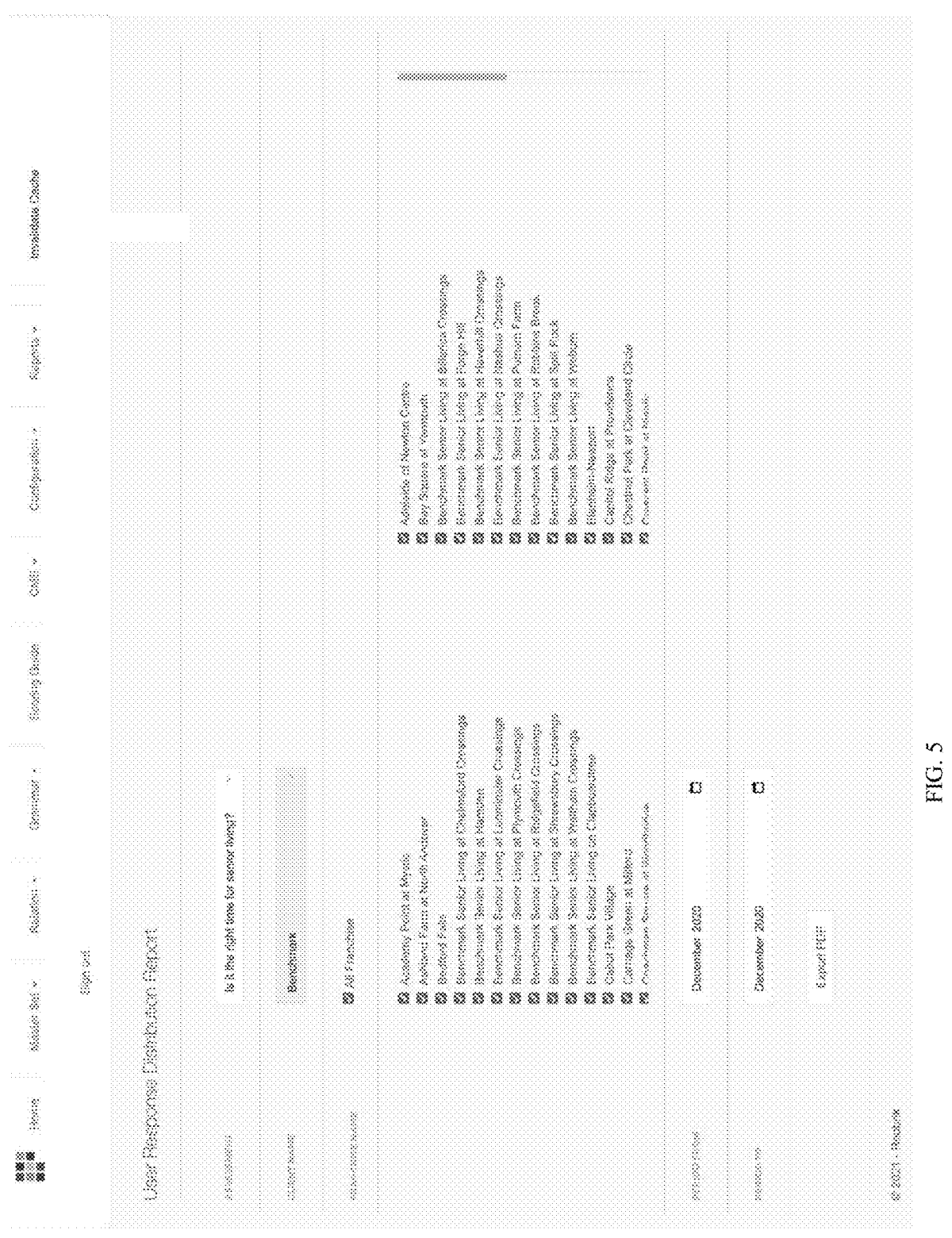

FIG. 4A illustrates an embodiment of the care decision platform wherein the platform is operable to be customized for a care service provider. FIG. 4B illustrates an embodiment of the care decision platform wherein the platform allows for customized passwords and access options for a care service provider. The customization options include assessments, number of communities, access methods, host domains, and passwords. In one embodiment, the platform of the present invention is operable to be integrated with a platform of the care service provider via an application programming interface (API). In another embodiment, the platform of the present invention sends emails containing the customer data to the care service provider. The emails are sent on a regular basis. Alternatively, the emails are triggered by the customer data. In one embodiment, the care decision platform is operable to aggregate, sort, and/or filter the customer data according to the needs of the care service provider. In one embodiment, the care decision platform is operable to be integrated with automated marketing services, live chat, and/or bot chat. FIG. 5 illustrates an embodiment wherein the care decision platform includes a provider interface. The provider interface is operable to apply filters to the customer data, e.g., a franchise filter. The provider interface is further operable to display the customer data related to a customer assessment in a user response distribution report.

Figure 6:
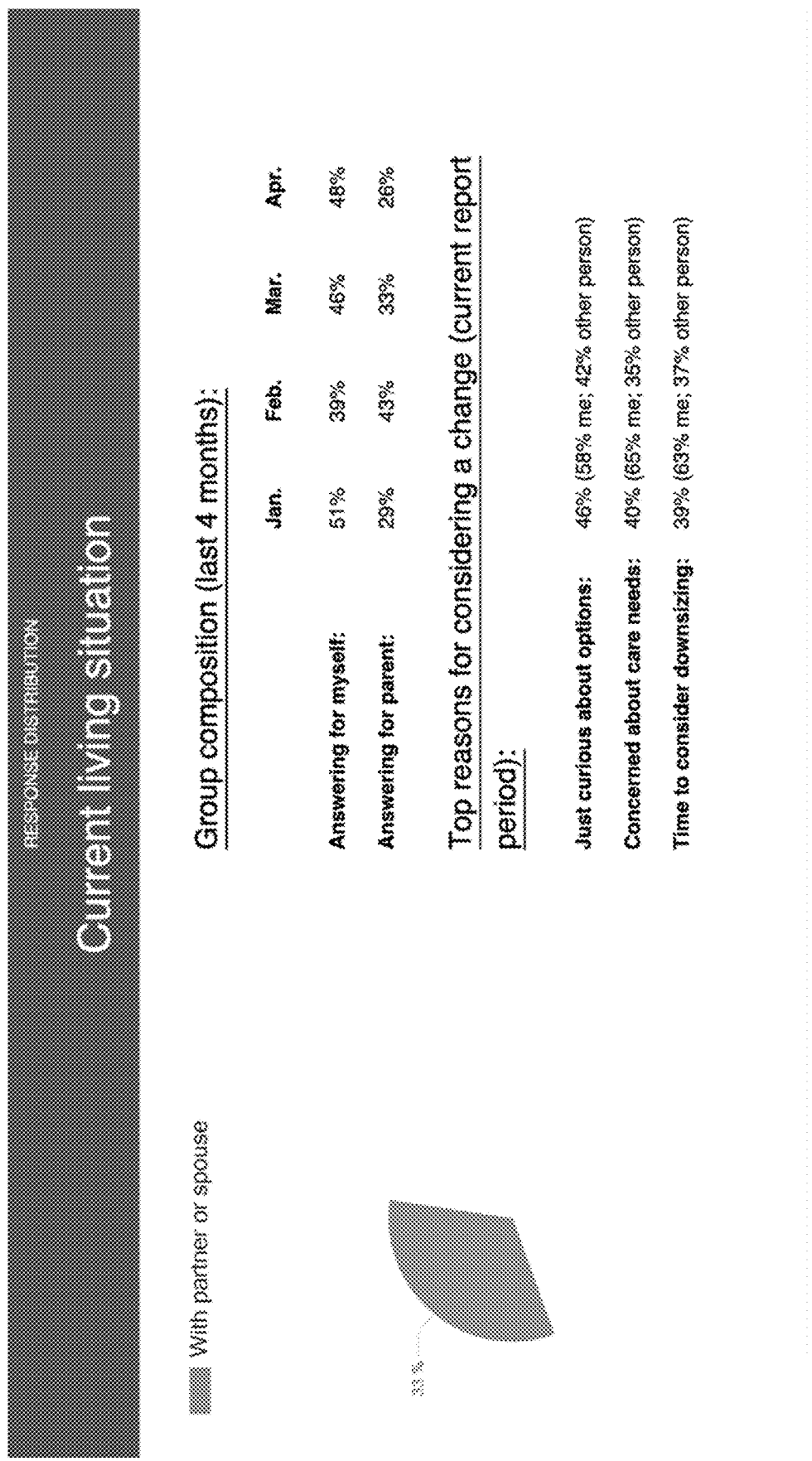
FIG. 6 illustrates an example embodiment of a data report of the present invention.

FIG. 6 illustrates an embodiment of a data slicing report produced by the care decision platform. The care decision platform is operable to aggregate, slice, and disaggregate data according to a variety of parameters. In the non-limiting example of FIG. 6, the data slicing report shows the top reasons for considering a change in current living situation depending on whether a customer is filling out an assessment for themselves or whether the child of the customer is filling out the assessment for their parent. The data in the data slicing report of FIG. 6 indicate that the largest percentage of respondents to the assessment are "just curious about options" regarding living situations. However, disaggregated percentages show that for respondents who are more serious about care needs and/or downsizing, it is more likely that customers themselves are the respondents rather than children of the customer (stakeholders). The care decision platform is operable to use this data in determining the at least one score (e.g., a score measuring fitness for changing current living situation), the at least one next step, and the curriculum. The care decision platform is also operable to report and investigate change over time. For example, the data slicing report of FIG. 6 shows that the percentage of respondents answering for themselves decreased between January and February. The care decision platform is operable to pull additional customer data and historical data to determine potential reasons for the change. The care decision platform is also operable to identify, monitor, and/or report trends in real time or near real time.

Figure 7:
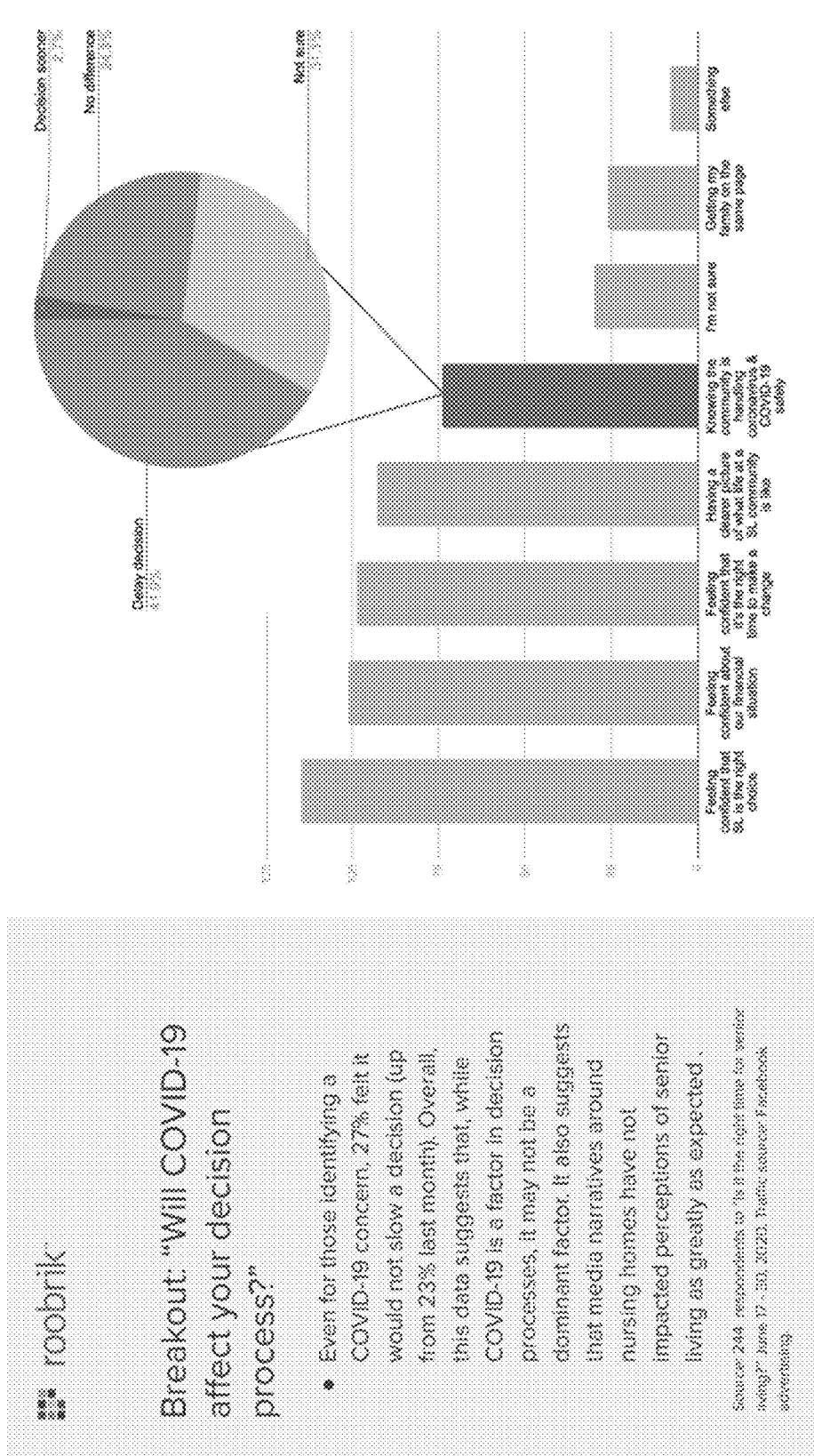
FIG. 7 illustrates an alternative embodiment of a data report of the present invention.

FIG. 7 is another embodiment of a data report created by the care decision platform. The care decision platform is operable to collect and analyze data regarding a specific breakout question wherein the breakout question pertains to current events, public health trends, new information, a factor affecting health outcomes, and/or a demographic indicator. In one embodiment, the assessment platform is operable to modify assessments to include the breakout question and/or questions related to the breakout question. In the example of FIG. 7, the assessment platform included a question about the COVID-19 pandemic to better assess customer attitudes and decision-making as a result of the pandemic. The care decision platform is operable to generate a hypothesis and/or a conclusion regarding the breakout question according to the aggregated data. In one embodiment, the care decision platform is further operable to spotlight a portion of the data and provide more detail automatically. Alternatively, the care decision platform is operable to accept user input to create and/or modify data visualizations. The care decision platform is also operable to record traffic source data, or how customers are accessing the assessments provided by the assessment platform, e.g., through web advertising, direct communication, referrals, web searches. The traffic source data is part of the historical data. The care decision platform is then operable to analyze the traffic source data in order to determine measures of efficacy and conversion as well as trends in the traffic source data. In one embodiment, the care decision platform is operable to create traffic data reports for a care service provider. Alternatively, the care decision platform is operable to use the traffic source data to inform future scores, next steps, and/or curricula.

In one embodiment, the platform of the present invention is universal and can be applied to a plurality of care service providers. The platform is operable to share the customer data between the plurality of care service providers and adapt the customer data to create separate curricula for each of the plurality of care service providers based on a single set of customer data. Each curriculum is customized for the services and needs of the corresponding care service provider. Alternatively, the platform is operable to create a consolidated curriculum, wherein the consolidated curriculum includes next steps and services corresponding to a plurality of care service provider options. The presentation and delivery of the curriculum is also operable to be customized individually by each care service provider. As a non-limiting example, the care decision platform collects data from the customer through a first care service provider. The care decision platform then generates a first curriculum of next steps for the customer to take in communicating with and considering the services of the first care service provider. The customer can also access a second care service provider using a universal set of login credentials wherein the second care service provider also integrates the care decision platform. The care decision platform then creates a second curriculum of next steps for the customer to take in communicating with and considering the services of the second care service provider without needing to repeat the data collection. The first curriculum differs from the second curriculum in order to adapt to differences in available services and goals between the first care service provider and the second care service provider. In one embodiment, the care decision platform selectively shares a portion of customer data and/or a portion of the curriculum to a care service provider.

In one embodiment, the present invention is operable to identify leads and collect data about the leads. The leads are potential customers who are not yet committed to a care service provider. The present invention is operable to identify the leads from sources including but not limited to content marketing responses, advertising responses, conferences, marketing agencies, referrals, lead aggregators, and/or financial institutions. Alternatively, the present invention is operable to identify the leads through general website and/or platform usage, including usage of websites and platforms not related to the care decision platform. In one embodiment, the platform is operable to selectively share data about a lead to the care service provider. If the lead opts in and/or requests contact, the data about the lead is transmitted to the care service provider regardless of the results of the assessment. In one embodiment, the scoring engine is operable to calculate a score for a lead wherein the score assesses how likely it is that the lead will become a customer based on data collected about the lead. In another embodiment, the platform is operable to generate a curriculum for converting the lead into a customer. The conversion process includes optimizing user experience (UX) at key conversion points (e.g., start, select customer, sign-up points) to increase start rate. In another embodiment, the conversion process is adjusted based on the source of traffic to the care service provider platform (e.g., organic traffic, retargeted traffic, paid traffic, and/or social traffic).

In one embodiment, the curriculum includes communication strategies and communication steps for customer relationship management. The communication steps include but are not limited to updates, reminders, suggestions, and/or questions, delivered via a website, an email, a live chat, an app notification, a search result, an in-person communication, a phone call, and/or a video call. In one embodiment, the communication strategies and steps are designed to encourage customers to continue interacting with the curriculum and/or the care service provider. In another embodiment, the communication strategies and steps are designed to engage with customers who have stopped interacting with the curriculum and/or the care service provider. The care decision platform is operable to utilize behavioral psychology practices, consumer psychology practices, and health decision sciences in order to determine the communication strategies and steps for customer relationship management.

FIG. 8 illustrates an example embodiment of a communication between the care decision platform and the customer wherein the communication is an email. The communication is customized for the customer by including information about their history with the care decision platform including but not limited to past assessments, steps taken, previous outcomes, previous engagements, indications of interest, and/or other information tailored to the concerns of the customer. A goal of the communication is to encourage shared decision making wherein the communication explains pros and cons of different options and provides data to enable an informed decision. In one embodiment, the communication provides data that the customer is lacking. The care decision platform is operable to determine the data that the customer is lacking using the customer data as well as historical data.

Figure 9:
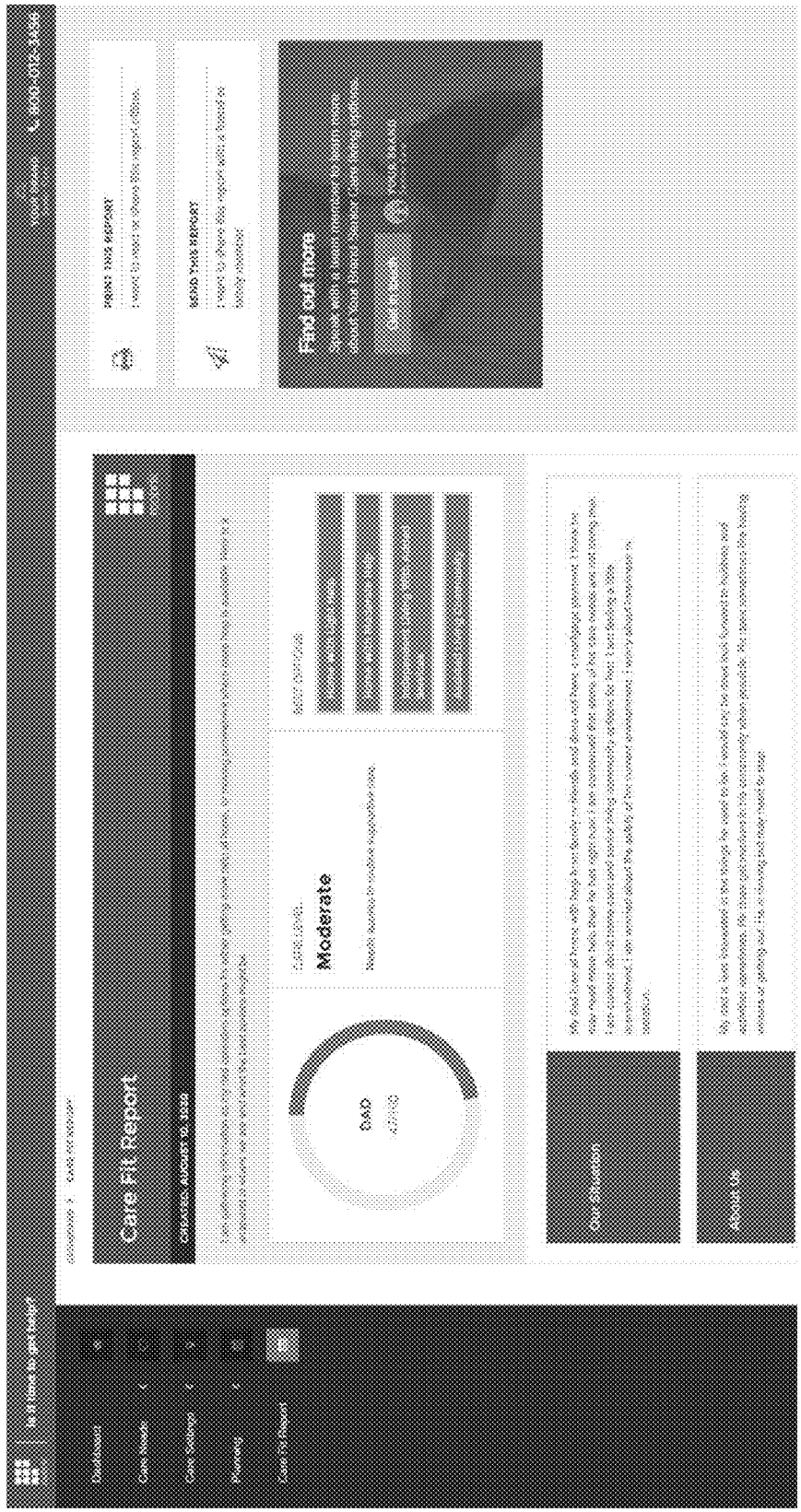
FIG. 9 illustrates an example embodiment of a client report of the present invention.

In one embodiment, the care decision platform of the present invention is further operable to perform data analytics. As a non-limiting example, the platform is operable to generate client reports for the care service provider. The content of the client reports includes but is not limited to a number of visitors, a number of leads, a number of customers, a conversion rate, an average age, a medical summary, and/or a timeline. The care decision platform is operable to provide a client report to both the customer and a care service provider. Alternatively, the care decision platform is operable to generate care fit reports wherein the care fit reports include scores, recommendations, and/or next steps for a customer regarding at least one care service and/or at least one lifestyle choice. In one embodiment, the client report includes a care fit report. FIG. 9 illustrates an example embodiment of a care fit report with best options for a customer given their situation, as determined by the assessment platform and the data collection platform. In one embodiment, the client report outlines a customer journey through a plurality of touchpoints, wherein the touchpoints include but are not limited to customer outcomes, engagements, and/or sales process milestones. In one embodiment, the client report includes customer outcomes that were not facilitated by the care decision platform but that still occurred. Alternatively, the platform is operable to track deployment of the care decision platform, e.g., with Google Tag Manager. In one embodiment, the platform is operable to create an interactive dashboard and business intelligence reports using data from a plurality of data sources including the customer and the care service provider. For example, the platform is operable to integrate Power BI tools.

Nurturing Decision Coach

In a preferred embodiment, the care decision platform includes a decision coach wherein the decision coach is operable to create guided paths to decision making. The decision coach is operable to be integrated with the care decision platform as a supplement to marketing automation platforms. The decision coach is further operable to incorporate principles and/or best practices of behavioral sciences and/or psychology, consumer psychology, medical decision sciences, and/or customer relationship management. The decision coach creates a set of personalized results for a customer based on the customer data, the at least one score, the at least one recommendation, and the curriculum. In an embodiment wherein a plurality of stakeholders is participating in the care decision platform for a single customer, the decision coach is operable to create multiple sets of personalized results wherein each set of personalized results corresponds to one of the plurality of stakeholders. Alternatively, the care decision platform is operable to create an aggregate set of personalized results based on aggregated input from the plurality of stakeholders. Advantageously, the aggregate set of personalized results is a more comprehensive view of the customer. The set of personalized results is provided with a consistent tone, style, and approach when compared to care decision platform and the care service provider. In one embodiment, the set of personalized results includes the client report. In one embodiment, the decision coach selectively presents a portion of the set of personalized results to a user. In one embodiment, the user is the customer receiving care from the care service provider. Alternatively, the user is at least one stakeholder involved in care decision making for the customer. The selective presentation of the set of personalized results is dynamically adjusted to increase user engagement with the care decision platform. The decision coach is further operable to selectively present a portion of the set of personalized results to the care service provider.

Figure 10:
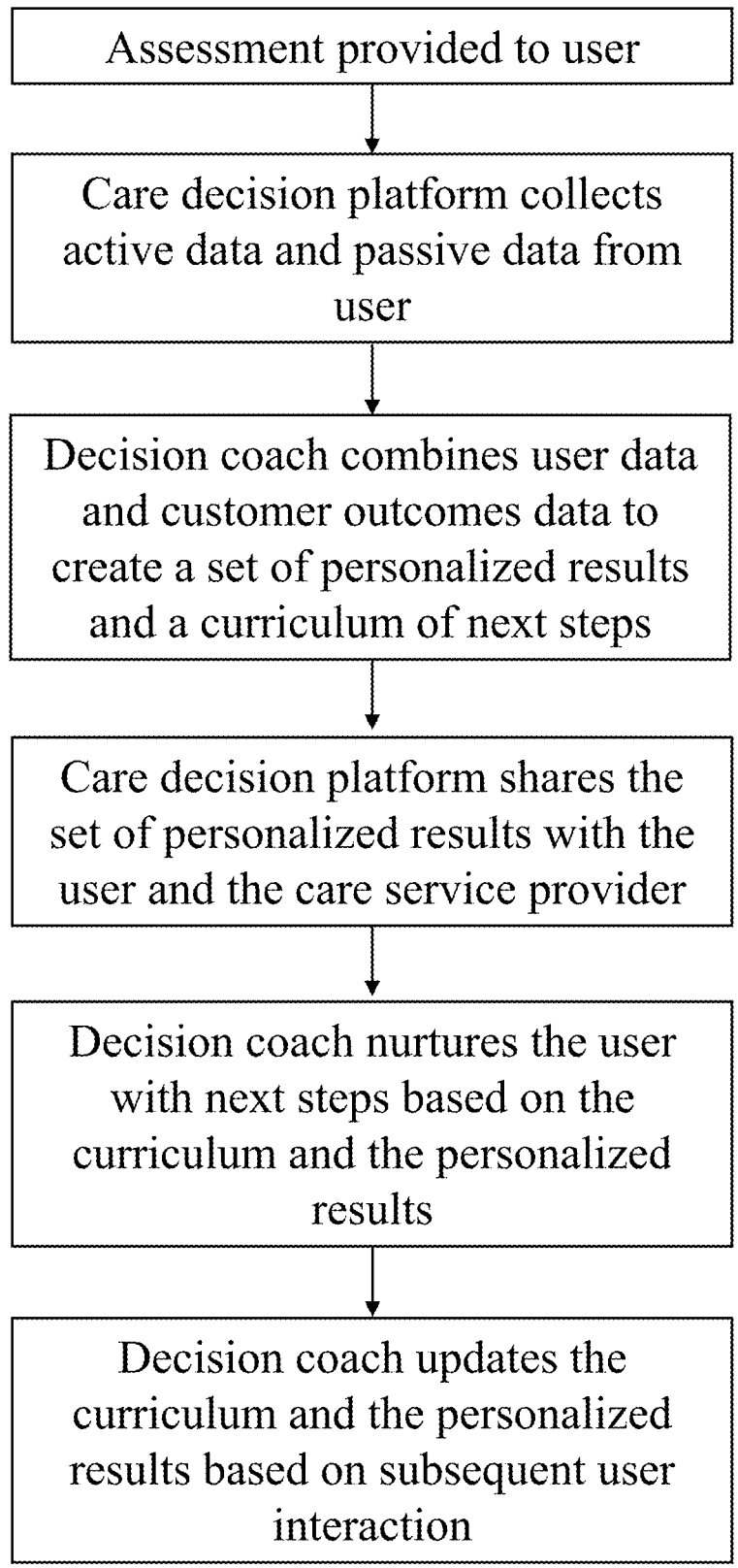
FIG. 10 illustrates an embodiment of a workflow of the present invention.
Figure 11:
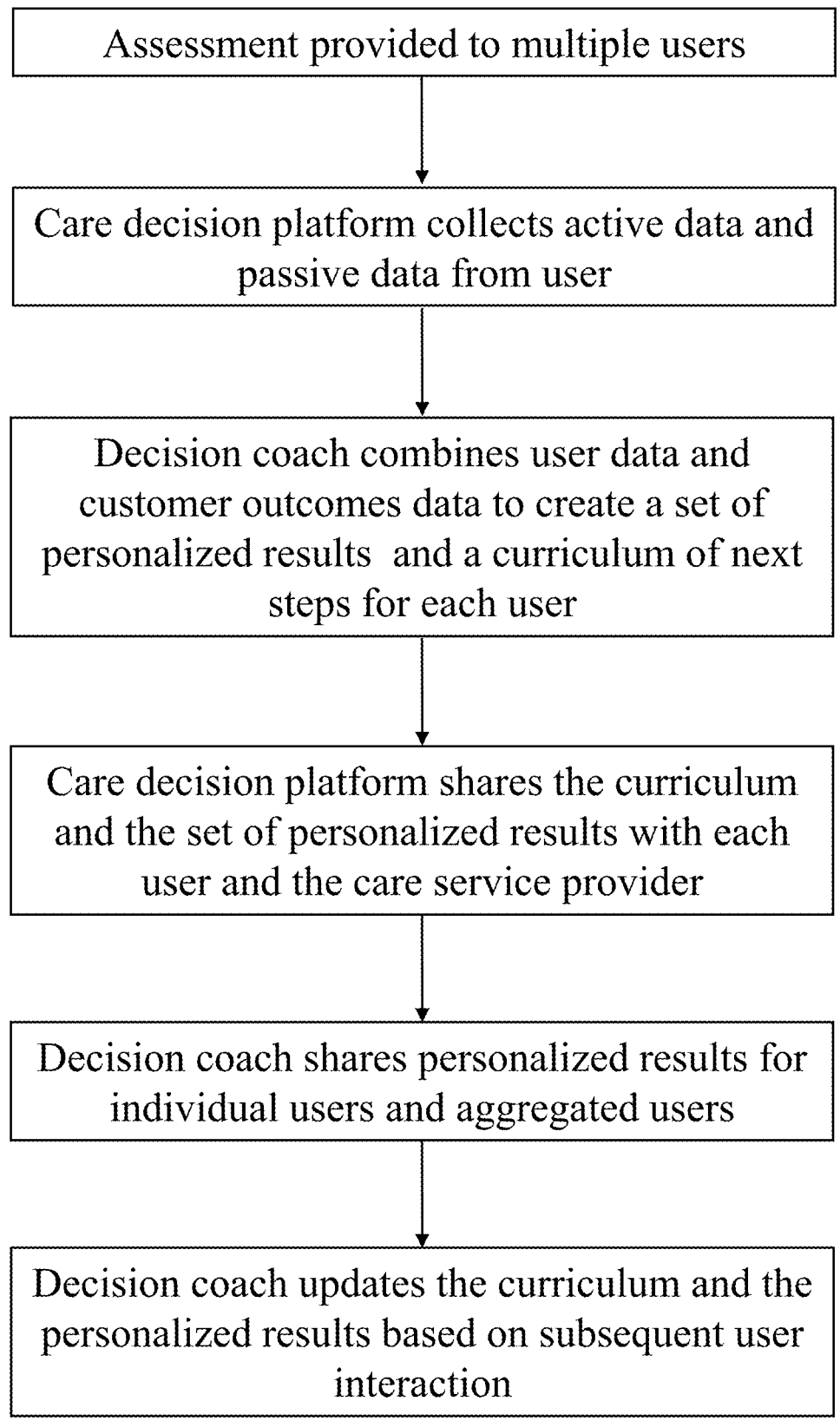
FIG. 11 illustrates an alternative embodiment of a workflow of the present invention.
Figure 12:
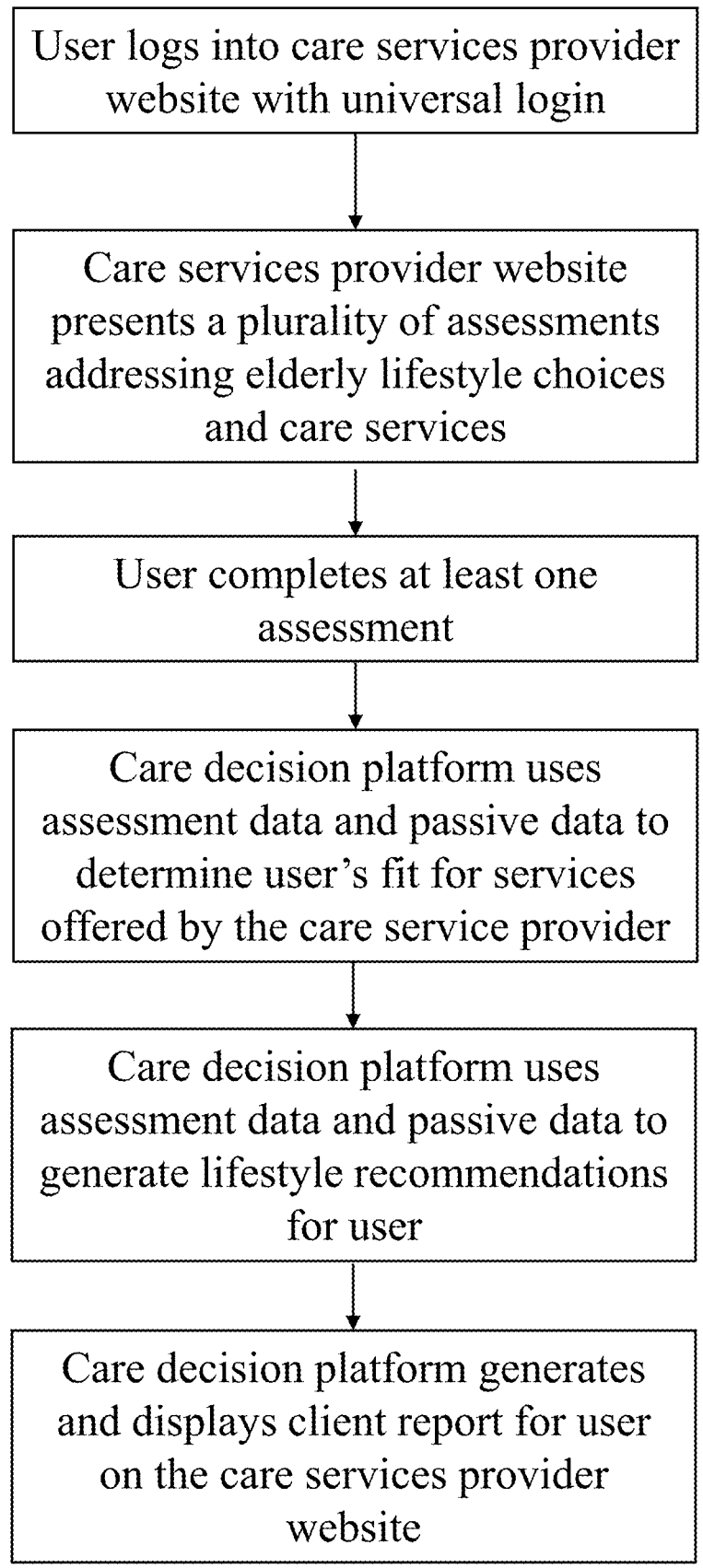
FIG. 12 illustrates an embodiment of the user experience workflow of the care decision platform.
Figure 13:
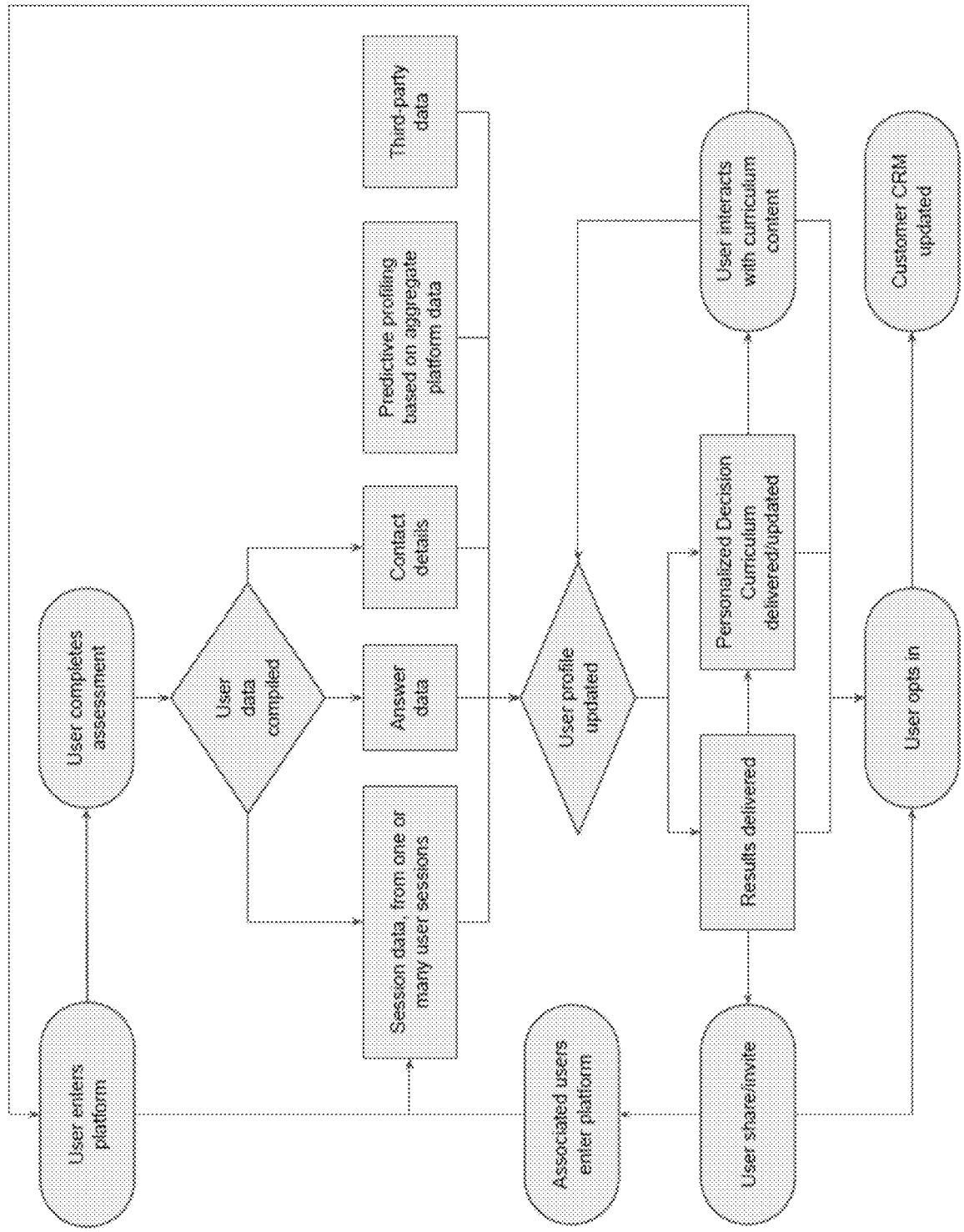
FIG. 13 illustrates yet another embodiment of a workflow of the present invention.

FIG. 10 illustrates one embodiment of a workflow of the care decision platform wherein the user is the customer interested in receiving services from the care service provider. FIG. 11 illustrates an alternative workflow of the care decision platform wherein the user is a plurality of stakeholders providing customer data on behalf of a customer. FIG. 12 illustrates an embodiment of the user experience workflow of the care decision platform. The care decision platform is integrated onto the website of a care services provider. The care decision platform then designs the curriculum and the recommendations based on the customer data and the care services provider integrating the care decision platform. The recommendations and curriculum are presented to the customer through the client report. FIG. 13 illustrates yet another embodiment of the user experience workflow wherein the care decision platform updates a user profile and wherein the user profile informs the curriculum. The care decision platform incorporates user-facing interactions with CRM recommendations. The care decision platform is also operable to include data from a plurality of users and a plurality of user sessions to update the user profile and the curriculum.

The decision coach is operable to deliver at least one nurturing step to the user (e.g., a customer, a stakeholder) wherein the at least one nurturing step is operable to help the user make a proactive care decision. In one embodiment, the at least one nurturing step is an email. In another embodiment, the at least one nurturing step is a notification, a prompt, a phone call, a text message, a live chat, a physical notice, a video call, and/or an in-person communication. In one embodiment, the nurturing step is the next step in the curriculum designed to improve likelihood of at least one customer outcome. In another embodiment, the nurturing step is a plurality of options that the user can take. The decision coach delivers the curriculum according to the timeline included in the curriculum. In the embodiment wherein the user is a plurality of stakeholders, the decision coach is operable to deliver a plurality of next steps simultaneously. Each curriculum is designed based on the customer data received from each stakeholder. The decision coach is operable to follow the curriculum corresponding to each stakeholder in delivering the plurality of next steps. For example, the decision coach is operable to send a text message reminder to a first stakeholder and set up an in-person appointment for a second stakeholder according to the communication preferences of each stakeholder. As an alternate example, the decision coach is operable to send a two-week reminder to a first stakeholder and a three-week reminder to a second stakeholder for the same event based on customer outcomes data. Alternatively, the decision coach is operable to design an aggregate curriculum based on the customer data from the plurality of stakeholders wherein the aggregate curriculum resolves dissent in the customer data.

Figure 14:
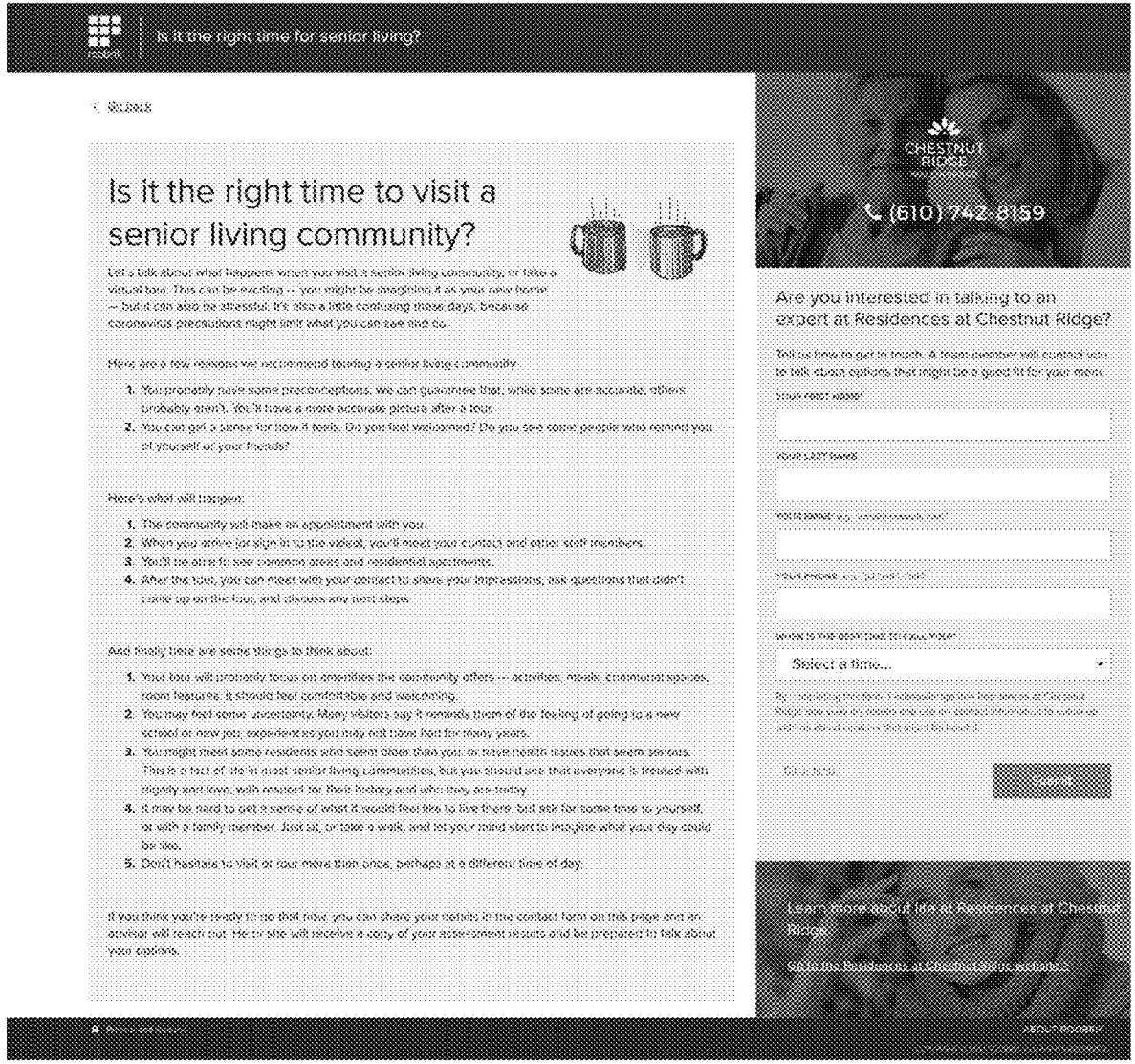
FIG. 14 illustrates an embodiment of a nurturing step of the present invention.

FIG. 14 illustrates one embodiment of the at least one nurturing step delivered to the user by the decision coach. In this example embodiment, the decision coach is operable to set expectations and provide next steps for the user based on historical data. The step is a nurturing step in that it is designed based on the historical data and the customer data to reduce user stress and uncertainty. The at least one nurturing step in this embodiment further includes prompts and suggestions to improve customer outcomes. Additionally, the care decision platform is operable to prompt the user to initiate direct contact with a care service provide in order to further improve customer outcomes.

In one embodiment, the present invention includes a graphical user interface (GUI) wherein the GUI is operable to display the set of personalized results on an interactive display device. The interactive display device includes but is not limited to a computer, a television, a mobile device, a tablet, a cell phone, and/or a wearable device. In another embodiment, the set of personalized results is delivered via an audio device, e.g., a smart speaker. The decision coach is further operable to receive input from the user via the GUI. In one embodiment, the input from the user is a response to the set of personalized results and/or an engagement with the care service provider. In another embodiment, the input is new customer data.

Figure 15:
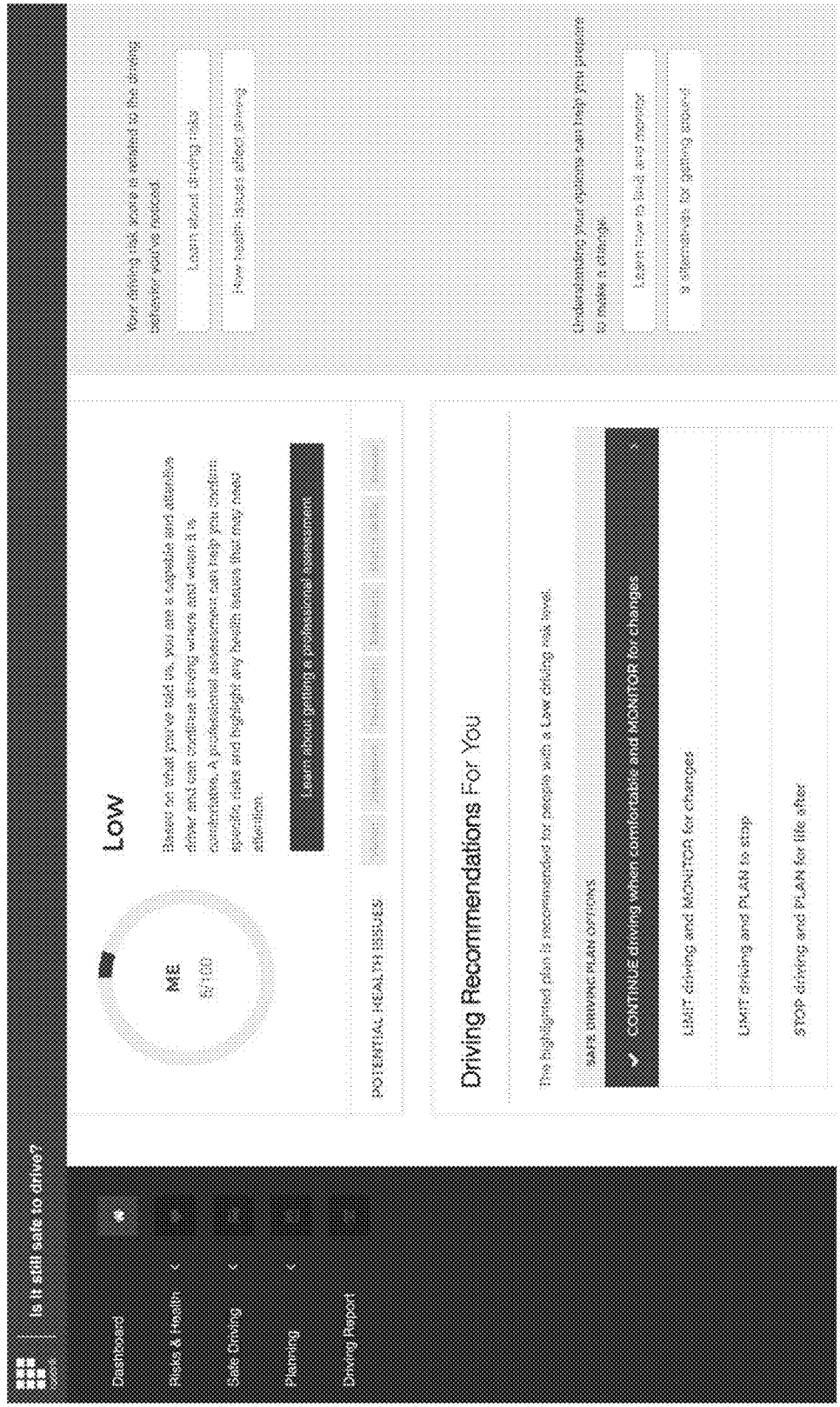
FIG. 15 illustrates an embodiment of a set of personalized results of the present invention.
Figure 16:
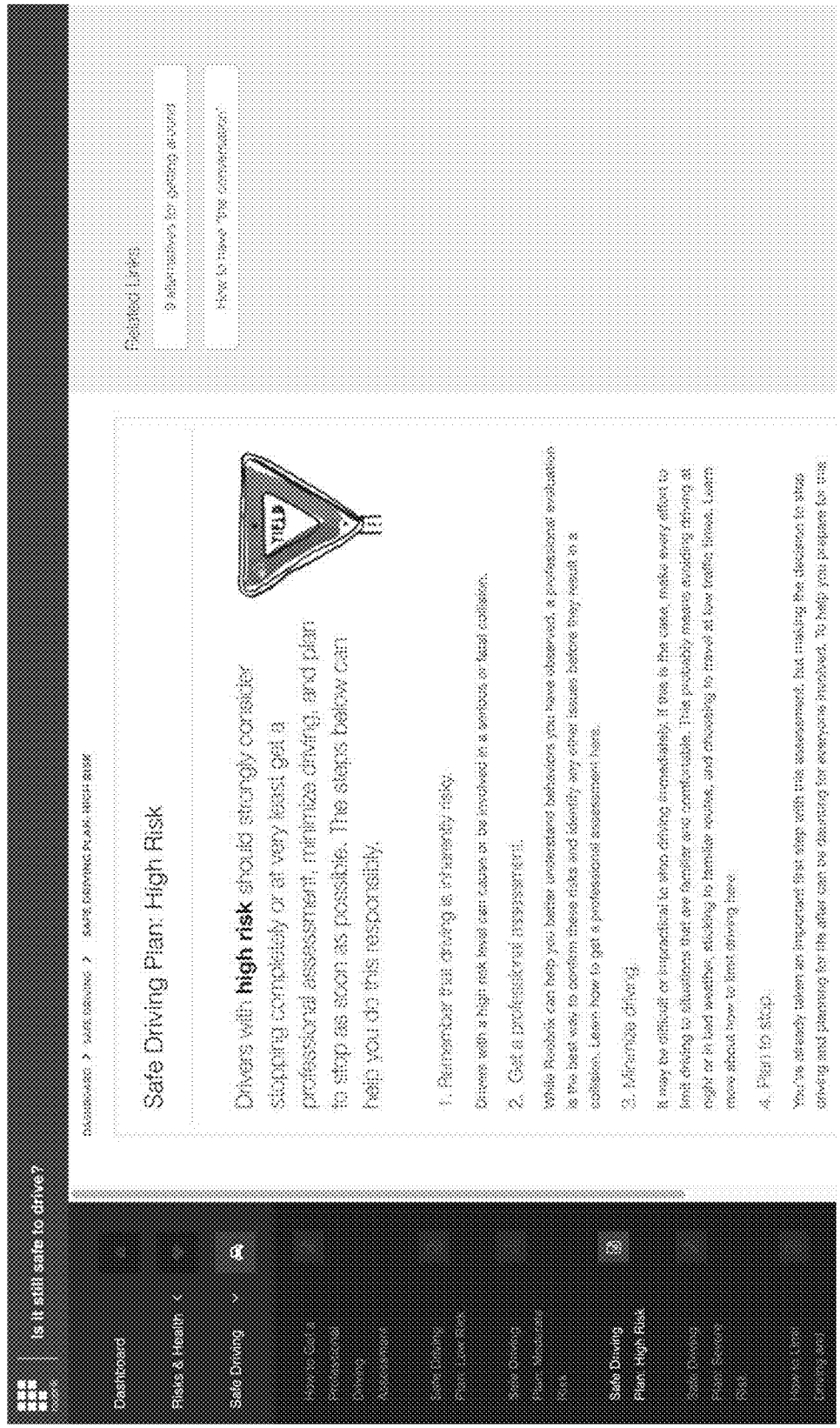
FIG. 16 illustrates an alternative embodiment of data presented by the decision coach of the present invention.

FIG. 15 illustrates an example embodiment of a set of personalized results delivered to a customer by the decision coach based on an assessment regarding driving safety. In this embodiment, the care decision platform used the assessment data, the customer data, and historical data to determine a driving risk score for the customer. The set of personalized results includes the driving risk score, an explanation of the driving risk score, as well as recommendations for the customer. Advantageously, the curriculum further includes practical details on how to follow through and complete the recommendations. FIG. 16 illustrates an embodiment wherein the care decision platform is operable to display additional generic information regarding the assessment. Advantageously, the generic information gives the customer more context and potential future steps.

Advantageously, the decision coach overcomes deficiencies of marketing automation platforms by using both passive and active customer data collected by the care decision platform and the at least one score, the at least one recommendation, and the curriculum. The set of personalized results and the curriculum are thus created using more than self-reported customer data. The use of historical and ongoing outcomes data in developing the curriculum provides a more accurate set of personalized results with higher chance of successful customer outcomes. Additionally, the decision coach is operable to segment the customer data in order to create more effective workflows and campaigns using historical customer outcomes data and data about the customer service provider. In one embodiment, the decision coach is operable to choose between the plurality of paths provided by the curriculum.

In a preferred embodiment, the care decision platform is dynamic. The decision coach is operable to recalculate the at least one score and re-determine the at least one recommendation in response to new customer data. The decision coach is further operable to automatically adjust the curriculum and the set of personalized results including the care fit report based on new customer data. The new customer data includes updates and/or changes to previously provided customer data including quantitative data, qualitative data, medical history, passive customer data, and/or active data. The new customer data further includes but is not limited to the customer outcomes, e.g., a contact, a follow-up, a tour, a pre-sale engagement, a sales process milestone, a sale engagement, a contract date, and/or a move-in. In one embodiment, the decision coach updates the curriculum based on the new customer data in order to improve customer health outcomes. Alternatively, the decision coach updates the curriculum based on the new customer data in order to improve engagement between the customer and the care service provider. In one embodiment, the decision coach updates the curriculum in real time or near-real time. In one embodiment, the care decision platform is operable to prompt the user for new customer data, e.g., through follow-up assessments. The prompts are made based on the customer data and/or actions taken by the user. Alternatively, the care decision platform prompts the user for new customer data according to a predetermined schedule. In one embodiment, the care decision platform is operable to gather the customer data over a variable period of time from at least one user and/or at least one stakeholder. In one embodiment, the care decision platform is operable to analyze changes and/or identify trends in the customer data. Historical customer outcomes data further includes changes in historical customer outcomes data and/or trends in historical customer outcomes data. The care decision platform is then operable to use the changes in the customer data for predictive analytics, score generation, recommendation, and/or curriculum development.

In one embodiment, the decision coach is operable to adjust a timing of next steps based on the new customer data. As a non-limiting example, a user takes a longer than average amount of time to respond to a follow-up from the decision coach. As a result, the decision coach accelerates the delivery of the next step after the user response in order to better capture the interest of the user and prevent further delays in engagement. In another embodiment, the decision coach is operable to bypass next steps based on the new customer data, thereby creating new paths. In yet another embodiment, the decision coach is operable to switch between the plurality of paths depending on the new customer data. Advantageously, the dynamic care decision platform is able to incorporate new data and adapt the curriculum and the set of personalized results to continue meeting the needs of the user and the care service provider.

Data Management

In one embodiment, the care decision platform includes a database wherein the database is geo-replicated for automatic failover between regions. The database includes but is not limited to the customer data, the historical data, and data about the care service provider. In one embodiment, sensitive data including personally identifiable information is password-protected. Alternatively, the care decision platform includes access roles and access policies. In one embodiment, the customer data is associated with a unique session. The database and architecture of the present invention are in one embodiment compliant with the Health Insurance Portability and Accountability Act of 1996 (HIPAA).

Figure 17:
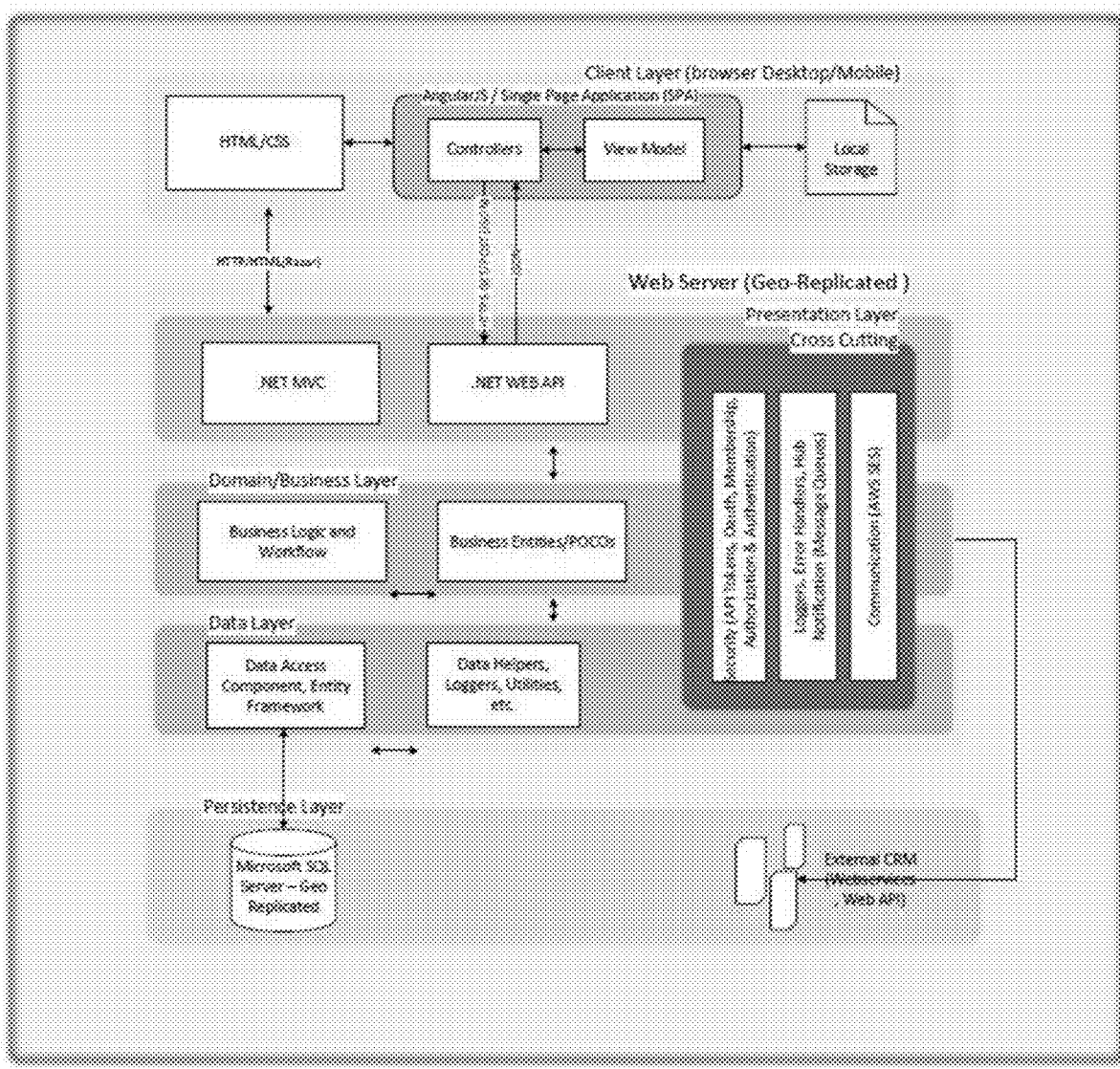
FIG. 17 illustrates an embodiment of the architecture of the present invention.

In one embodiment, the care decision platform is deployed on scalable multitier architecture. FIG. 17 depicts an example embodiment wherein the platform is deployed on three-tier architecture using the .NET framework of the Microsoft Technology Stack. In one embodiment, the care decision platform is hosted on a cloud-based service, e.g., Microsoft's Azure Cloud Services, for high availability and scalability.

Figure 18:
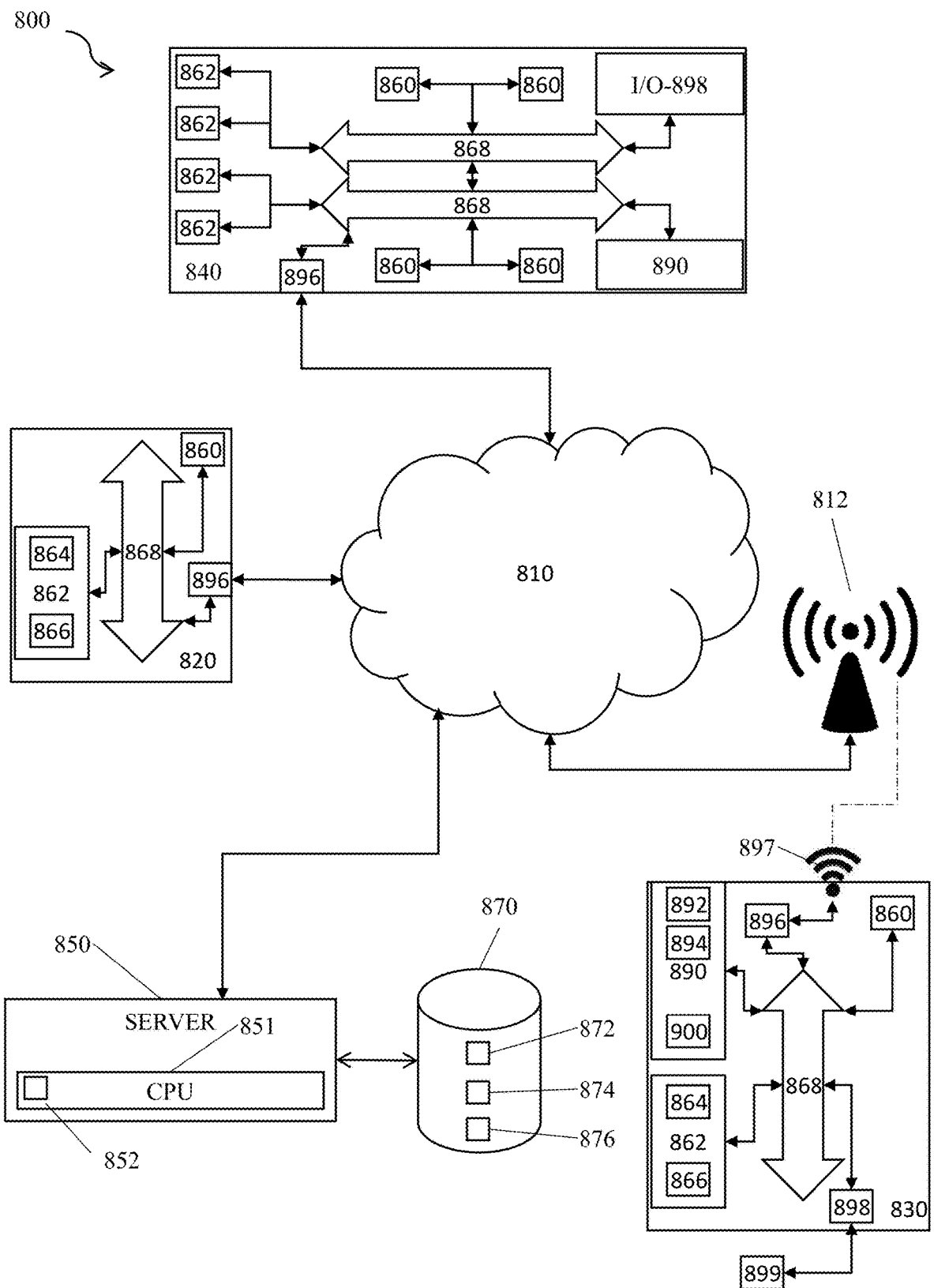
FIG. 18 is a schematic diagram of an embodiment of the present invention.

FIG. 18 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 18, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 18, is operable to include other components that are not explicitly shown in FIG. 18, or is operable to utilize an architecture completely different than that shown in FIG. 18. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

The above-mentioned examples are provided to serve the purpose of clarifying the aspects of the invention, and it will be apparent to one skilled in the art that they do not serve to limit the scope of the invention. By nature, this invention is highly adjustable, customizable and adaptable. The above-mentioned examples are just some of the many configurations that the mentioned components can take on. All modifications and improvements have been deleted herein for the sake of conciseness and readability but are properly within the scope of the present invention.

The invention claimed is:

1. A system for engaging with care service options and/or lifestyle choices, comprising:
at least one user device;
at least one cloud platform;
an assessment platform;
a data collection engine;
a scoring engine;
a recommendation engine; and
a decision coach;
wherein the at least one user device is operable for network communication with the at least one cloud platform;
wherein the assessment platform is operable to administer at least one assessment to at least one user account on at least one user device and receive assessment data in response to the at least one assessment;
wherein the assessment platform is operable to receive financial data about the at least one user account from a plurality of interested third party devices;
wherein the assessment platform is operable to receive data about the at least one user account from the plurality of interested third party devices;
wherein the data collection engine is operable to collect passive data from the at least one user device and combine the passive data, the data from the plurality of interested third party devices, the financial data, and the assessment data into user data, wherein the user data is in a standardized format;
wherein the data collection engine is operable to determine the location of the at least one user device using a global positioning system (GPS);
wherein the scoring engine is operable to generate at least one score based on the user data;
wherein the recommendation engine is operable to generate at least one recommendation based on the user data;
wherein the recommendation engine is operable to utilize the location of the at least one user device in generating the at least one recommendation;
wherein the decision coach is operable to design a curriculum of next steps based on the user data, the at least one score, and the at least one recommendation;
wherein the decision coach is operable to mark data disagreement between the passive data obtained from the at least one user device, the assessment data, and the data from the plurality of interested third party devices;
wherein the decision coach is operable to resolve the data disagreement;
wherein the recommendation engine is operable to incorporate aggregate data and/or predictive analytics to make recommendations for resolving areas of data disagreement, wherein the recommendations are based on previously effective steps for resolving areas of data disagreement;
wherein the decision coach is operable to deliver the curriculum to the at least one user account on the at least one user device;
wherein the decision coach is operable to dynamically adjust the curriculum based on updated user data; and
wherein the at least one cloud platform is operable to store the user data and the curriculum.

2. The system of claim 1, wherein the at least one user device is a wearable device, a mobile device, a tablet, a computer, a smart speaker, and/or a smart phone.

3. The system of claim 1, wherein the user data further includes sensor data.

4. The system of claim 1, wherein the user data further includes electronic health record (EHR) data and wherein the data collection engine is operable to integrate with an EHR platform.

5. The system of claim 1, wherein the passive data includes web analytics, urchin tracking module (UTM) parameters, date, time, online user behaviors, a completion rate, engagement metrics, response distribution, hypertext markup language (HTML) requests, and/or location information.

6. The system of claim 1, wherein the data collection engine is operable to apply at least one filter to the user data.

7. The system of claim 1, wherein the at least one score is a readiness for a care service option and/or a lifestyle choice.

8. The system of claim 1, wherein the assessment platform is operable to prompt the at least one user account on the at least one user device for the updated user data according to a schedule.

9. The system of claim 1, wherein the decision coach is operable to correlate a plurality of input data points with a plurality of outcome data points to design and/or adjust the curriculum.

10. The system of claim 1, wherein the decision coach is operable to design and/or adjust the curriculum using at least one machine learning algorithm.

11. The system of claim 1, wherein the decision coach is operable to design and/or adjust the curriculum using at least one predictive analytics model.

12. The system of claim 1, wherein the decision coach is further operable to design and/or adjust the curriculum using past user outcomes data.

13. The system of claim 1, wherein the curriculum includes a plurality of paths and wherein the decision coach is operable to choose one of the plurality of paths based on the updated user data.

14. The system of claim 1, wherein the decision coach is operable to adjust the curriculum based on the updated user data in real time or near real time.

15. A system for engaging with care service options and/or lifestyle choices, comprising:
- at least one user device;
- at least one cloud platform;
- an assessment platform;
- a data collection engine;
- a scoring engine;
- a recommendation engine; and
- a decision coach;
- wherein the at least one user device is operable for network communication with the at least one cloud platform;
- wherein the assessment platform is operable to administer at least one assessment to at least two user accounts on the at least one user device and receive assessment data from the at least two user accounts in response to the at least one assessment;
- wherein the assessment platform is operable to receive financial data about the at least two user accounts from a plurality of interested third party devices;
- wherein the assessment platform is operable to receive data about the at least one user account from the plurality of interested third party devices;
- wherein the data collection engine is operable to collect passive data associated with each of the at least two user accounts from the at least one user device and combine the passive data, the data from the plurality of interested third party devices, the financial data, and the assessment data into user data, wherein the user data is in a standardized format;
- wherein the data collection engine is operable to determine a length of time taken to answer at least one question of the at least one assessment by measuring a length of screen time of the at least one user device used to answer the at least one question of the at least one assessment and determine if at least one follow-up question is required;
- wherein the scoring engine is operable to generate at least one score based on the user data;
- wherein the recommendation engine is operable to generate at least one recommendation based on the user data;
- wherein the decision coach is operable to design at least one curriculum of next steps based on the user data, the at least one score, and the at least one recommendation;
- wherein the decision coach is operable to mark data disagreement between the passive data obtained from the at least one user device, the assessment data, and the data from the plurality of interested third party devices;
- wherein the decision coach is operable to resolve the data disagreement;
- wherein the recommendation engine is operable to incorporate aggregate data and/or predictive analytics to make recommendations for resolving areas of data disagreement, wherein the recommendations are based on previously effective steps for resolving areas of data disagreement;
- wherein the decision coach is operable to deliver the at least one curriculum on the at least one user device;
- wherein the decision coach is operable to deliver a second curriculum to the plurality of interested third party devices;
- wherein the delivery of the at least one curriculum is accompanied by at least one notification;
- wherein the decision coach is operable to dynamically adjust the at least one curriculum based on updated user data; and
- wherein the at least one cloud platform is operable to store the user data and the at least one curriculum.

16. The system of claim 15, wherein the decision coach is operable to deliver the at least one curriculum to each of the at least two user accounts simultaneously.

17. The system of claim 15, wherein the decision coach is operable to design and adjust an aggregate curriculum based on the user data, the at least one score, and the at least one recommendation.

18. A method for engaging with care service options and/or lifestyle choices, comprising:
- an assessment platform administering at least one assessment to at least one user account on at least one user device and receiving assessment data in response to the at least one assessment;
- the assessment platform receiving financial data about the at least one user account from a plurality of interested third party devices;
- the assessment platform receiving data about the at least one user account from the plurality of interested third party devices;
- a data collection engine collecting passive data from the at least one user device and combining the assessment data, the data from the plurality of interested third party devices, the financial data, and the passive data into user data, wherein the user data is in a standard format;
- the data collection engine determining a length of time take to answer at least one question of the at least one assessment by measuring a length of screen time of the at least one user device used to answer the at least one question of the at least one assessment and determine if at least one follow-up question is required;

a scoring engine generating at least one score based on the user data;
a recommendation engine generating at least one recommendation based on the user data;
a decision coach designing at least one curriculum of next steps based on the user data, the at least one score, and the at least one recommendation;
the decision coach marking data disagreement between the passive data obtained from the at least one user device, the assessment data, and the data from the plurality of interested third party devices;
the decision coach resolving the data disagreement;
the recommendation engine incorporating aggregate data and/or predictive analytics to generate recommendations for resolving the areas of data disagreement, wherein the recommendations are based on previously effective steps for resolving areas of data disagreement;
the decision coach delivering the at least one curriculum on the at least one user device;
wherein the delivery of the at least one curriculum in accompanied by at least one notification;
the decision coach delivering a second curriculum to the plurality of interested third party devices;
the decision coach dynamically adjusting the at least one curriculum based on updated user data; and
at least one cloud platform storing the user data and the at least one curriculum;
wherein the at least one user device is in network communication with the at least one cloud platform.

19. The method of system 18, further comprising the decision coach designing and adjusting the at least one curriculum using at least one machine learning algorithm.

20. The system of claim 1, wherein the assessment platform is operable to utilize a voice analyzer to detect an emotional and/or a mental state of a user associated with the at least one user device.

* * * * *